(12) United States Patent
Foley et al.

(10) Patent No.: US 6,663,622 B1
(45) Date of Patent: Dec. 16, 2003

(54) SURGICAL DEVICES AND METHODS FOR USE IN TISSUE ABLATION PROCEDURES

(75) Inventors: Frederick J. Foley, Bedford, NH (US); James S. Sharrow, Bloomington, MN (US); Lorraine E. Reeve, Dexter, MI (US); Thomas G. Adelman, West Baldwin, ME (US); Michael F. Hoey, Shoreview, MN (US)

(73) Assignee: Iotek, Inc., Minneapolis, MN (US)

( * ) Notice: Subject to any disclaimer, the term of this patent is extended or adjusted under 35 U.S.C. 154(b) by 1 day.

(21) Appl. No.: 09/649,998

(22) Filed: Aug. 28, 2000

Related U.S. Application Data

(60) Provisional application No. 60/217,304, filed on Jul. 11, 2000, provisional application No. 60/206,081, filed on May 22, 2000, provisional application No. 60/190,411, filed on Mar. 17, 2000, and provisional application No. 60/181,895, filed on Feb. 11, 2000.

(51) Int. Cl.$^7$ ................................................ A61B 18/18
(52) U.S. Cl. .......................................... 606/34; 606/41
(58) Field of Search .......................... 606/32–35, 37–42, 606/45–50; 607/96, 100, 102, 101, 115, 116, 122; 600/374

(56) References Cited

U.S. PATENT DOCUMENTS

| | | |
|---|---|---|
| 3,534,733 A | 10/1970 | Phipps et al. |
| 3,542,022 A | 11/1970 | Bartnik |

(List continued on next page.)

FOREIGN PATENT DOCUMENTS

| | | |
|---|---|---|
| EP | 0 157 888 | 10/1985 |
| EP | 0 319 394 | 6/1989 |

(List continued on next page.)

OTHER PUBLICATIONS

Lowe et al., "Non–Blood–Contacting Riventricular Support: Direct Mechanical Ventricular Actuation," Operative Techniques in Thoracle and Cardiovascular Surgery, vol. 1, No. 1, pp. 345–351, Nov. 1999.

(List continued on next page.)

*Primary Examiner*—Michael Peffley
(74) *Attorney, Agent, or Firm*—Shumaker & Sieffert, PA

(57) ABSTRACT

Devices and a method are provided to assist a surgeon in ablating conduction paths in tissue, such as a heart. A device can be configured to operate as a template that adheres to the tissue surface, and allows the surgeon to more easily sever the conduction path to form a lesion in a desired location. In particular, the template can be used to guide the surgeon's use of a surgical instrument along a desired ablation path. In some case, the template may incorporate hardware that structurally supports the instrument for travel along the ablation path. A surgical instrument such as an ablation probe, e.g., radio frequency, laser, ultrasonic, microwave, thermal, chemical, mechanical, or cryogenic ablation probe, may be used to sever the conduction paths. Measurements made substantially contemporaneously with the conduction path ablation operation may be used to evaluate whether the desired degree of ablation has been achieved. The device may also incorporate feedback to compare the desired degree of conduction path ablation with the measured degree, and may deactivate the surgical instrument when the desired degree has been achieved. In some cases, the template device can be configured to provide local stabilization of organ tissue, particularly for a moving organ such as a beating heart. In other cases, the template device may provide little or no stabilization, but provide a guide structure for placement of the ablation probe in the same frame of motion as the moving tissue. Also, for some applications, the template device may be arranged to facilitate application of other therapeutic devices, such as diagnostic probes, pacing leads, and drug delivery devices, to the surface of a moving organ.

37 Claims, 21 Drawing Sheets

U.S. PATENT DOCUMENTS

| | | | |
|---|---|---|---|
| 3,590,815 A | 7/1971 | Schiff | |
| 3,608,540 A | 9/1971 | Sartorius | |
| 3,613,672 A | 10/1971 | Schiff | |
| 3,640,270 A | 2/1972 | Hoffman | |
| 3,786,801 A | 1/1974 | Sartorius | |
| 3,811,443 A | 5/1974 | Dickinson, III et al. | |
| 3,926,192 A | 12/1975 | Van Maren | |
| 3,952,737 A | 4/1976 | Lipfert et al. | |
| 4,048,990 A | 9/1977 | Goetz | |
| 4,362,157 A | 12/1982 | Keeth | |
| 4,543,949 A | 10/1985 | Goepp et al. | |
| 4,596,566 A | 6/1986 | Kay | |
| 4,732,148 A | 3/1988 | L'Esperance, Jr. | |
| 4,736,749 A | 4/1988 | Lundback | |
| 4,973,300 A | 11/1990 | Wright | |
| 4,991,574 A | 2/1991 | Pocknell | |
| 5,111,832 A | 5/1992 | Saksena | |
| 5,119,804 A | 6/1992 | Anstadt | |
| 5,226,908 A | 7/1993 | Yoon | |
| 5,248,304 A | 9/1993 | Vigdorchik et al. | |
| 5,259,836 A | 11/1993 | Thurmond et al. | |
| 5,282,785 A | 2/1994 | Shapland et al. | |
| 5,336,252 A | 8/1994 | Cohen | |
| 5,341,807 A * | 8/1994 | Nardella | 600/381 |
| 5,403,312 A | 4/1995 | Yates et al. | |
| 5,409,008 A | 4/1995 | Svenson et al. | |
| 5,423,878 A | 6/1995 | Franz | |
| 5,437,658 A | 8/1995 | Muller et al. | |
| 5,447,529 A | 9/1995 | Marchlinski et al. | |
| 5,472,438 A | 12/1995 | Schmit et al. | |
| 5,484,407 A | 1/1996 | Osypka | |
| 5,497,771 A | 3/1996 | Rosenheimer | |
| 5,499,971 A | 3/1996 | Shapland et al. | |
| 5,507,741 A | 4/1996 | L'Esperance, Jr. | |
| 5,509,890 A | 4/1996 | Kazama | |
| 5,536,243 A | 7/1996 | Jeyendron | |
| 5,545,123 A | 8/1996 | Ortiz et al. | |
| 5,553,612 A | 9/1996 | Lundback | |
| 5,562,658 A | 10/1996 | Long | |
| 5,562,721 A | 10/1996 | Marchlinski et al. | |
| 5,575,810 A | 11/1996 | Swanson et al. | |
| 5,593,405 A | 1/1997 | Osypka | |
| 5,651,378 A | 7/1997 | Matheny et al. | |
| 5,665,105 A | 9/1997 | Furnish et al. | |
| 5,676,662 A | 10/1997 | Fleischhacker et al. | |
| 5,725,521 A | 3/1998 | Mueller | |
| 5,727,569 A | 3/1998 | Benetti et al. | |
| 5,730,757 A | 3/1998 | Benetti et al. | |
| 5,738,683 A | 4/1998 | Osypka | |
| 5,749,892 A | 5/1998 | Vierra et al. | |
| 5,762,458 A | 6/1998 | Wang et al. | |
| 5,776,154 A | 7/1998 | Taylor et al. | |
| 5,779,661 A | 7/1998 | Stephen et al. | |
| 5,782,746 A | 7/1998 | Wright | |
| 5,799,661 A | 9/1998 | Boyd et al. | |
| 5,807,243 A | 9/1998 | Vierra et al. | |
| 5,807,388 A | 9/1998 | Jeevanandam et al. | |
| 5,810,721 A | 9/1998 | Mueller et al. | |
| 5,836,311 A | 11/1998 | Borst et al. | |
| 5,843,019 A | 12/1998 | Eggers et al. | |
| 5,843,020 A | 12/1998 | Tu et al. | |
| 5,843,154 A | 12/1998 | Osypka | |
| 5,855,583 A | 1/1999 | Wang et al. | |
| 5,865,730 A | 2/1999 | Fox et al. | |
| 5,868,763 A | 2/1999 | Spence et al. | |
| 5,871,017 A | 2/1999 | Mayer | |
| 5,871,495 A | 2/1999 | Mueller | |
| 5,871,496 A | 2/1999 | Ginn et al. | |
| 5,875,782 A | 3/1999 | Ferrari et al. | |
| 5,876,340 A | 3/1999 | Tu et al. | |
| 5,885,271 A | 3/1999 | Hamilton et al. | |
| 5,888,247 A | 3/1999 | Benetti | |
| 5,891,017 A | 4/1999 | Swindle et al. | |
| 5,893,848 A | 4/1999 | Negus et al. | |
| 5,894,843 A | 4/1999 | Benetti et al. | |
| 5,899,425 A | 5/1999 | Corey Jr. et al. | |
| 5,906,607 A | 5/1999 | Taylor et al. | |
| 5,910,150 A | 6/1999 | Saadat | |
| 5,913,876 A | 6/1999 | Taylor et al. | |
| 5,916,213 A | 6/1999 | Haissaguere et al. | |
| 5,921,979 A | 7/1999 | Kovac et al. | |
| 5,927,284 A | 7/1999 | Borst et al. | |
| 5,931,848 A | 8/1999 | Saadat | |
| 5,935,141 A | 8/1999 | Weldon | |
| 5,938,660 A | 8/1999 | Swartz et al. | |
| 5,941,893 A | 8/1999 | Saadat | |
| 5,944,730 A | 8/1999 | Nobles et al. | |
| 5,944,736 A | 8/1999 | Taylor et al. | |
| 5,947,125 A | 9/1999 | Benetti | |
| 5,947,896 A | 9/1999 | Sherts et al. | |
| 5,951,581 A | 9/1999 | Saadat et al. | |
| 5,957,835 A | 9/1999 | Anderson et al. | |
| 5,964,754 A | 10/1999 | Osypka | |
| 5,971,976 A | 10/1999 | Wang et al. | |
| 5,971,980 A * | 10/1999 | Sherman | 606/34 |
| 5,972,020 A | 10/1999 | Carpentier et al. | |
| 5,976,069 A | 11/1999 | Navia et al. | |
| 5,976,123 A | 11/1999 | Baumgardner et al. | |
| 5,976,164 A | 11/1999 | Bencini et al. | |
| 5,978,695 A | 11/1999 | Greenwald et al. | |
| 5,984,864 A | 11/1999 | Fox et al. | |
| 5,999,835 A | 12/1999 | Osypka | |
| 6,007,486 A | 12/1999 | Hunt et al. | |
| 6,007,523 A | 12/1999 | Mangosong | |
| 6,012,457 A | 1/2000 | Lesh | |
| 6,013,027 A | 1/2000 | Khan et al. | |
| 6,015,378 A | 1/2000 | Borst et al. | |
| 6,015,427 A | 1/2000 | Mueller et al. | |
| 6,017,304 A | 1/2000 | Vierra et al. | |
| 6,019,722 A | 2/2000 | Spence et al. | |
| 6,024,740 A | 2/2000 | Lesh et al. | |
| 6,032,672 A | 3/2000 | Taylor | |
| 6,036,641 A | 3/2000 | Taylor et al. | |
| 6,066,139 A * | 5/2000 | Ryan et al. | 606/50 |
| 6,088,614 A * | 7/2000 | Swanson | 600/510 |
| 6,139,538 A | 10/2000 | Houghton et al. | |
| 6,146,379 A * | 11/2000 | Fleischman et al. | 600/374 |
| 6,183,468 B1 * | 2/2001 | Swanson et al. | 606/40 |
| 6,206,827 B1 | 3/2001 | Chin et al. | 600/217 |
| 6,231,585 B1 | 5/2001 | Takahashi et al. | |
| 6,256,540 B1 * | 7/2001 | Panescu et al. | 607/122 |
| 6,290,644 B1 | 9/2001 | Green, II et al. | |
| 6,290,699 B1 | 9/2001 | Hall et al. | |
| 6,302,880 B1 * | 10/2001 | Schaer | 606/41 |
| 6,306,085 B1 | 10/2001 | Farascioni | |
| 6,314,962 B1 | 11/2001 | Vaska et al. | |
| 6,314,963 B1 | 11/2001 | Vaska et al. | |
| 6,315,717 B1 | 11/2001 | Benetti et al. | |
| 6,322,558 B1 | 11/2001 | Taylor et al. | |
| 6,332,881 B1 | 12/2001 | Carner et al. | |
| 6,423,057 B1 * | 7/2002 | He et al. | 606/34 |
| 2001/0031961 A1 | 10/2001 | Hooven | |
| 2001/0041827 A1 | 11/2001 | Spence et al. | |
| 2002/0002372 A1 | 1/2002 | Jahns et al. | |

FOREIGN PATENT DOCUMENTS

| | | | |
|---|---|---|---|
| EP | 0 502 485 | 9/1992 | |
| EP | 0 791 330 A2 | 8/1997 | A61B/17/02 |
| EP | 0 993 806 A2 | 4/2000 | |

| | | | | |
|---|---|---|---|---|
| WO | WO 97/26828 | 7/1997 | | |
| WO | WO 98/37814 | 9/1998 | | |
| WO | WO 99/60929 | 12/1999 | | |
| WO | WO 99/60930 | 12/1999 | | |
| WO | WO 00/10466 | 3/2000 | | |
| WO | WO 00/62680 | 10/2000 | | |
| WO | WO 00/74574 | 12/2000 | | |
| WO | WO 01/12248 | 2/2001 | | |
| WO | WO 01/17437 A3 | 3/2001 | | |
| WO | WO 01/17437 A2 | 3/2001 | ........... | A61B/17/02 |
| WO | WO 01/80755 | 11/2001 | | |

OTHER PUBLICATIONS

Baue et al., "Mechanical Ventricular Assistance in Man," Supplement II to Circulation, vols. XXXVII and XXXVIII, pp. II–33–II36, Apr., 1968.

Nierich et al., "Heart Displacement During Off–Pump CABG: How Well Is It Tolerated?" The Society of Thoracic Surgeons, (Ann Thorac Surg 2000;70:466–72, Aug. 2000.

Borst et al., *Circulation*, 1999, 99:1400–1403.

"Cardiology Device Update," Nov. 15, 1999, Merrill Lynch.

* cited by examiner

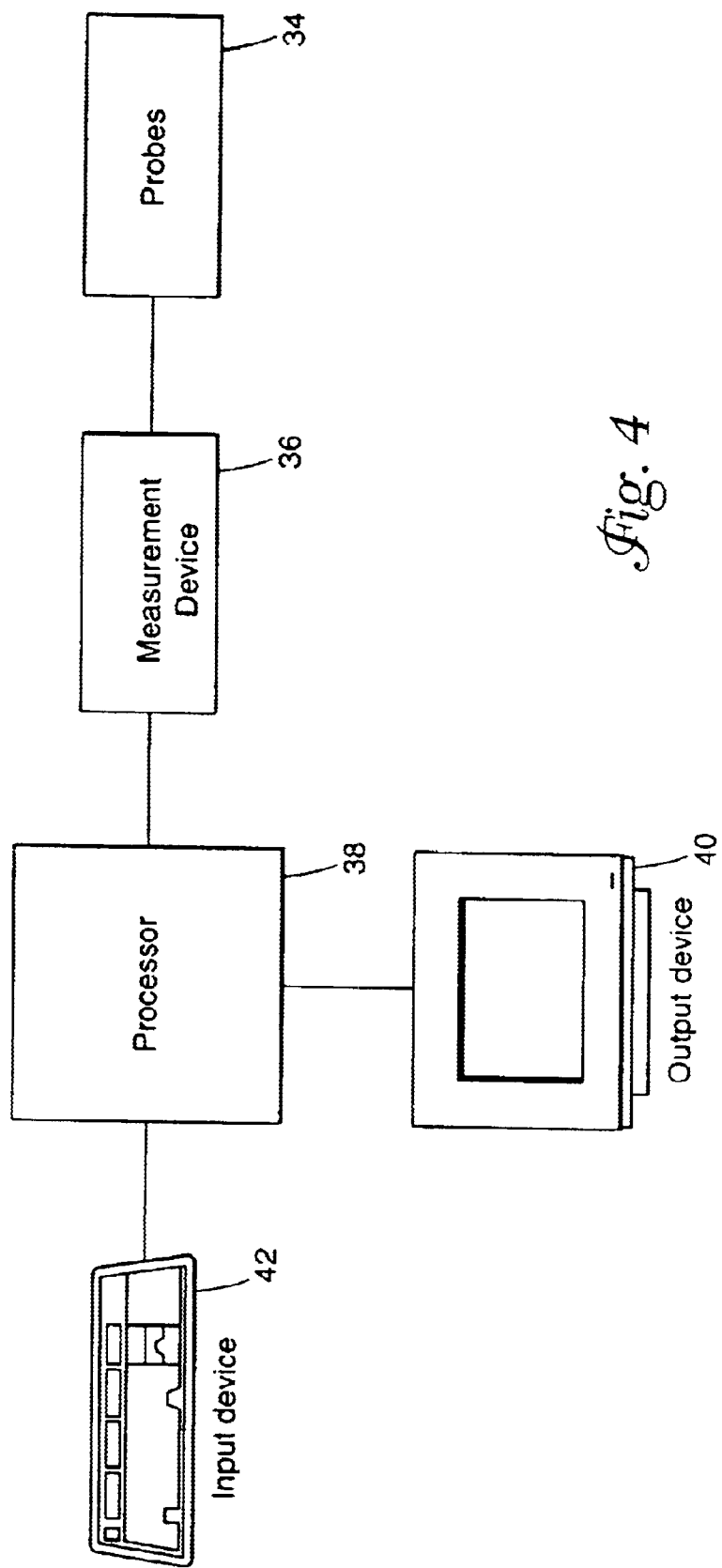

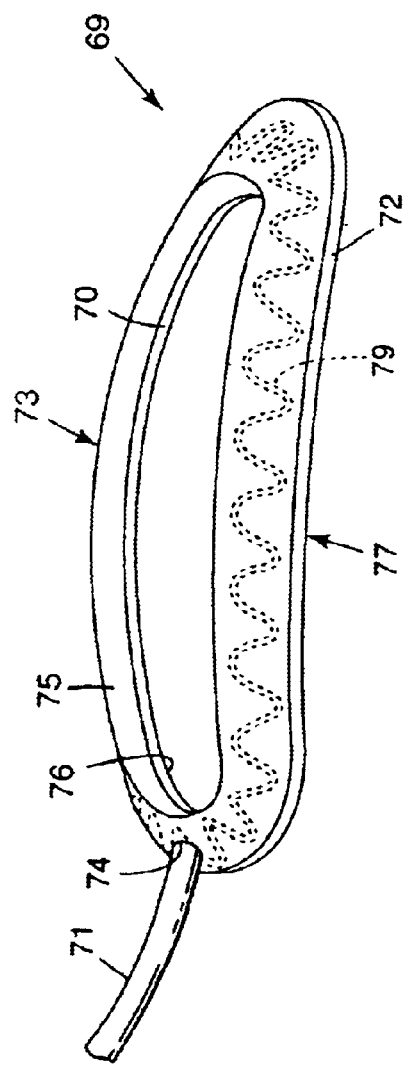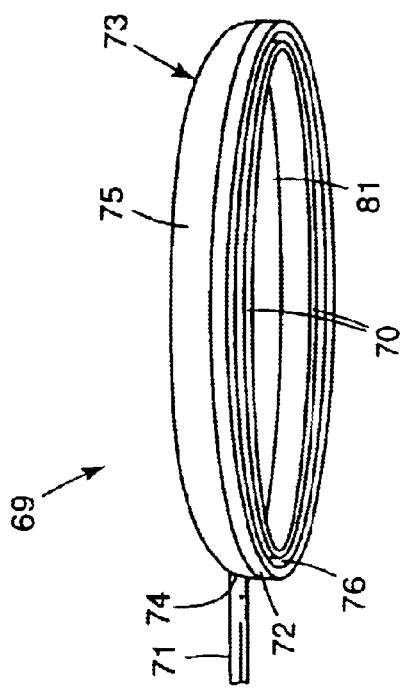

SURGICAL DEVICES AND METHODS FOR USE IN TISSUE ABLATION PROCEDURES

RELATED APPLICATIONS

This application claims priority from U.S. Provisional Application Serial No. 60/217,304, filed Jul. 11, 2000; U.S. Provisional Application Serial No. 60/206,081, filed May 22, 2000; U.S. Provisional Application Serial No. 60/190,411, filed Mar. 17, 2000; and U.S. Provisional Application Serial No. 60/181,895, filed Feb. 11, 2000, the entire content of each of which is incorporated herein by reference.

TECHNICAL FIELD

The invention generally relates to surgical devices and, more particularly, to surgical devices and methods for use in procedures performed on moving tissue.

BACKGROUND

Some forms of surgery involve ablation to kill tissue in an organ in order to achieve a therapeutic result. Ablation can be achieved by various techniques, including the application of radio frequency energy, lasers, cryogenic probes, and ultrasound. Thus, the term "ablation," as used herein refers to any of a variety of methods used to kill tissue within an organ. To be successful, ablation treatment may require considerable precision. The surgeon must target a particular region, and be careful not to cause unnecessary trauma to other areas of the patient's body near the target area. Just as important, the surgeon must be confident that the procedure within the target area has been appropriately performed. For example, the surgeon may need to determine whether the tissue has been ablated to an appropriate degree. The surgery may be made more difficult if the target area is moving.

One such surgical procedure in which a surgeon may wish to ablate moving tissue is an operation to correct an abnormal heartbeat. To function efficiently, the heart atria must contract before the heart ventricles contract. As blood returns to the heart and enters the atria, blood also flows through the atrioventricular (AV) valves and partially fills the ventricles. Following an electrical excitation by the sinoatrial (SA) node, the atria contract in unison, expelling blood into the ventricles to complete ventricular filling. The ventricles then become excited and contract in unison. Ventricular contraction ejects the blood out of the heart. Blood ejected from the right ventricle enters the pulmonary arteries for oxygenation by the lungs, and blood ejected from the left ventricle enters the main aorta and is distributed to the rest of the body. If the timing of cardiac functions is impaired, such as by the atria not contracting in unison or by the ventricles contracting prematurely, then the operation of the heart is impaired.

The synchronization of heart functions is initiated by an excitation from the SA node, which is the heart's natural pacemaker. The excitation propagates along an interatrial pathway, extending from the SA node in the right atrium to the left atrium. The excitation then spreads across gap junctions throughout the atria, causing the atria to contract in unison. The excitation further travels down an internodal pathway to the AV node, which transmits the excitation to the ventricles along the bundle of His and across the myocardium via the Purkinje fibers. In an aging heart, the atria may stretch, and the conduction paths by which the excitations travel may become lengthened. As a result, the excitations have a longer distance to travel, and this may affect the timing of the heart contractions and may create an arrhythmia. The term "arrhythmia" is used to describe any variation from normal rhythm and sequence of excitation of the heart.

One form of arrhythmia is atrial fibrillation. Atrial fibrillation is characterized by chaotic and asynchronized atrial cell contractions resulting in little or no effective blood pumping into the ventricle. Ventricular contractions are not synchronized with atrial contractions, and ventricular beats may come so frequently that the heart has little time to fill with blood between beats. Atrial fibrillation may occur if conduction blocks form within the tissue of the heart, causing the electrical excitations to degenerate into flurries of circular wavelets, or "reentry circuits," which interfere with atrial activity. Initiation or maintenance of atrial fibrillation may be facilitated if atria become enlarged. Atrial enlargement increases the time required for the electrical impulse to travel across the atria. This allows sufficient time for the cells that contracted initially to repolarize and allows the re-entry circuit to be maintained.

One surgical procedure for treating some forms of arrhythmia is to disrupt conduction paths in the heart tissue by severing the paths at selected regions of the atrial myocardium. Selective disruption of the conduction pathways permits impulses to propagate from the SA node to activate the atria and the AV node, but prevents the propagation of aberrant impulses from other anatomic sites in the atria. Severing may be accomplished, for example, by incising the full thickness of the myocardial tissue followed by closing the incision with sutures. The resultant scar permanently disrupts the conduction paths. As an alternative, permanent lesions, in which tissue is killed, can be created by ablation. The ablation process involves creating a lesion that extends from the top surface of the myocardium to the bottom surface (endocardial surface). Thus, the purpose of ablation is to create one or more lesions that sever certain paths for the excitations while keeping other paths intact. In the case of atrial fibrillation, for example, the lesions may interrupt the reentry circuit pathways while leaving other conduction pathways open. By altering the paths of conduction, the synchronization of the atrial contractions with the ventricular contractions may be restored. A plurality of lesions may be needed to achieve the desired results.

Incision through the myocardium, referred to as the "maze procedure," requires suturing to restore the integrity of the myocardium, and exposes the patient to considerable risk and morbidity. In contrast, thermal or other forms of ablation can create effective lesions without the need for sutures or other restorative procedures. Consequently, ablation can be performed more quickly and with far less morbidity. For these reasons, ablation is becoming a preferred method for severing conduction paths. The surgical ablation procedure may be performed during open-heart surgery. In a typical open-heart surgery, the patient is placed in the supine position. The surgeon must then obtain access to the patient's heart. One procedure for obtaining access is the median sternotomy, in which the patient's chest is incised and opened. Thereafter, the surgeon may employ a rib-spreader to spread the rib cage apart, and may incise the pericardial sac to obtain access to the cardiac muscle.

For some forms of open-heart surgery, the patient is placed on cardiopulmonary bypass (CPB) and the patient's heart is arrested. CPB is preferred for many coronary procedures because the procedure is difficult to perform if the heart continues to beat. CPB, however, entails trauma to the patient with attendant side effects and risks.

In some circumstances, the patient may be treated by a procedure less invasive than the procedure described above.

One such less invasive procedure may be a lateral thoracotomy. The heart may be accessed through a comparatively small opening in the chest and accessed through the ribs. In such a procedure, arrest of the patient's heart may not be feasible, and if the heart cannot be arrested, the surgery must be performed while the heart continues to beat. Other procedures for access to the heart include sternotomy, thoracoscopy, transluminal, or combinations thereof.

Once the surgeon has obtained access to the heart, ablation can be carried out with a probe that delivers ablative energy. The ablative energy may take the form of electromagnetic radiation generated by a laser or radio frequency antenna. Other techniques for achieving ablation include the application of ultrasound energy or very low temperature. For the procedure to be successful, the created lesions should sever the targeted conduction paths. Typically, the surgeon must create a lesion of a particular length to create the desired severance. The surgeon must also create a lesion of a particular depth in order to prevent the electrical impulses from crossing the lesion. In particular, when the myocardial tissue is ablated, the lesion must be transmural, i.e., the tissue must be killed in the full thickness of the myocardium to prevent conduction across the ablation line.

SUMMARY

The present invention is directed to surgical devices and methods useful in guiding surgical instruments during procedures on internal organs such as the heart. The device may take the form of a surgical "template" device that is attached to the surface of an organ. The device can be configured to facilitate surgical procedures such as tissue ablation. For example, a surgical template can be used as a guide for travel of a surgical or ablative probe along a path to aid a surgeon in ablation of tissue to sever conduction paths in the heart and thereby alleviate arrhythmia. A surgical template device may be especially useful in operations where the organ tissue being treated is moving, e.g., for so-called beating heart surgery. The surgical template device may be effective in providing local stabilization of the tissue to which the tissue ablation procedure is directed. The devices and methods also may find use in procedures in which the pertinent organ is not moving.

Alternatively, the device may be configured to provide little or no stabilization, but provide guide structure for placement of the ablation probe in the same frame of motion as the moving tissue. In some cases, the template may incorporate hardware that structurally supports the instrument for travel along the ablation path. The template devices and methods can be configured for application of other types of therapeutic devices, such as diagnostic probes, pacing leads, and drug delivery devices, to the surface of a moving organ. To promote adhesion, in some embodiments, the device may be equipped with a compliant, tacky material that forms a seal for contact with tissue. The device also may be equipped with one or more vacuum ports that make use of vacuum pressure to enhance the attachment to the organ tissue. Adhesion refers to the ability of the device to hold fast to an organ on a temporary basis, either with the benefit of an adhesive or vacuum pressure or both. The present invention also is directed to surgical devices and methods useful in determining the effectiveness of a tissue ablation procedure. In some embodiments, a sensor may be integrated with a surgical template device as described above to assist the surgeon by making measurements that gauge whether the surgical procedure has been satisfactorily performed. For example, the surgical device may be configured to measure the effectiveness of an ablation procedure in terms of ablation length, depth or width. For example, the sensor may measure electrical characteristics of the tissue proximate the target conduction paths, e.g., tissue impedance, tissue conduction velocity, or tissue conduction time, as an indication of the effectiveness of the procedure. The information obtained by the sensor can be used as the basis for feedback to the surgeon, e.g., in audible and/or visible form. Moreover, the sensor information can be used as feedback for the closed-loop control of the tissue ablation probe. The sensor may be employed independently of a surgical template device.

As a further aid to the surgeon, the surgical template device may include indicators such as visible markings that show the targeted length of the ablation. The visible markings can be used as a reference by the surgeon during movement of the ablation probe within the template area provided by the device. Also, the template device may include a structure that physically restricts the length of travel of the ablation probe, as well as the shape of the path along which the probe travels. In particular, the length indicator may include a stop structure that extends into the path for travel of the ablation device and is oriented for abutment with the ablation device. In some embodiments, for example, the ablation template device may provide a linear path for travel of the ablation probe. In other embodiments, however, the template device may define a non-linear, e.g., curved, path for travel of the ablation probe.

Further, the present invention is directed to surgical devices and methods for manipulation of the heart and local stabilization of heart tissue for a tissue ablation procedure. In this aspect, the present invention may make use of a surgical template device that provides not only a guide for a tissue ablation procedure but also a structure that provides local stabilization of heart tissue within the operative area. In some embodiments, the ablation template device may be accompanied by a surgical manipulation device that adheres to the heart tissue and enables manipulation of the heart to provide the surgeon with a desired access orientation for the procedure. The manipulation device may permit lifting, pushing, pulling, or turning of the pertinent organ to provide the surgeon with better access to a desired area. For both the template and manipulation device, to promote adhesion, a compliant, tacky interface material can be provided for contact with tissue, along with one or more vacuum ports for use of vacuum pressure.

In addition to providing a guide for a procedure, a template device and associated methods can be arranged to provide structure that supports instruments such as ablation probes, diagnostic probes, pacing leads, and drug delivery devices, for application to the surface of a moving organ and active guidance along a path. For some surgical procedures, it is necessary to bring surgical instruments into contact with the surface of a particular organ. In addition to the ablation application described above, one example is the placement of one or more electrodes within or in contact with organ tissue to deliver electrical impulses to the organ tissue for various purposes, such as a pacing to control the beating of the heart. Another example is the placement of a syringe needle to deliver a medicament to a specific location on an organ. Although all these procedures could be performed manually by the surgeon when the body cavity is opened during surgery, each is made more difficult when performed via a small opening in the body cavity, usually through an endoscopy port. Moreover, such procedures are particularly complicated when the surface of the pertinent organ is moving, as with a beating heart.

Recently, some types of cardiac surgery have been performed through access ports or rather small incisions in the rib cage, instead of in the open field created by cutting through the sternum (a sternotomy) and spreading open the rib cage with a mechanical device. In these situations, there are occasions when surgical devices (diagnostic, therapeutic, etc.) will need to be affixed to a particular location on the heart surface without direct contact of the human hand. This might also be done while the heart is still beating. There is an increasing frequency of coronary artery bypass surgery done on beating hearts to avoid the morbidity associated with stopping the heart and placing the patient on cardiopulmonary bypass. Some surgeries on the beating heart are also performed using the traditional sternotomy. Access procedures such as sternotomy, thoracotomy, thoracoscopy, and percutaneous transluminal are contemplated.

To facilitate such procedures, a template device is provided to fix a particular surgical tool or diagnostic or therapeutic device within a defined operative path for the tool or device. There are some surgical procedures performed on a beating heart, or other organ, that will require the fixation of a surgical instrument, diagnostic device or therapeutic device to accomplish a specific surgical procedure, diagnostic measurement, or delivery of some therapeutic product or method. This is particularly true when such procedures, measurements, or deliveries are performed under minimally invasive conditions, such as through narrow tubes or ports that penetrate the skin and enter the abdominal or thoracic cavities. Template devices and associated methods, in accordance with the present invention, are useful in guiding surgical instruments, certain diagnostic sensors, or mechanisms for delivery of medicaments on the surface of internal organs, such as the heart.

The template devices and methods are particularly useful in attaching such instruments to the surface of the beating heart without any additional manual assistance of the surgeon, thereby facilitating certain procedures carried out both in open and minimally invasive procedures. Notable features of the template device include conformability to the contours of the organ, such as the heart, the ability to fix the device in place using vacuum, mechanical pressure, or adhesives, and atraumatic attachment by virtue of specific soft polymeric interfaces and shapes. The template device can be configured to attach to various surfaces of the heart using a vacuum seal. This device provides two or more vacuum ports surrounded by a conformable, compressible silicone gel or elastomer. As in the ablation template, these seals contain integrated electrodes for sending and receiving an electrical signal for the purpose of measuring impedance or conductance time or velocity across tissue in a treatment area. The electrodes may be surface or interstitial. Also, the electrodes may be multipolar, e.g., bipolar. In some embodiments, a single electrode within the seal may be sufficient with a reference electrode located elsewhere. A vacuum port or other fluid removal device may be desirable to remove fluids from the chamber to avoid the effects of such fluids on the electrical performance of the electrode(s) or electrical ablation devices. The ports can be attached to a single or multiple independent vacuum lines.

In some embodiments of the invention, ablation is performed on the interior surfaces of the tissues. For example, an ablating instrument may be directed transluminally, such as by way of a catheter, near the ostia of the pulmonary veins in the left atrium of the heart. Following the ablation and creation of a lesion, electrodes delivered by the catheter may be used to measure the efficacy of the ablation.

For radio frequency ablation, for example, enclosed in the body of the device can be a channel in which is located a moveable cable housing a radio frequency (RF) antenna for delivery of RF energy to the myocardium. The device allows the RF antenna to be moved by a remote control unit on the distal end of the cable. The cable can be moved through its channel by the controller in response to feedback from the sensors on the vacuum seals. As a lesion becomes transmural in one location, the sensors detect either decreases in impedance or increases in conduction time. This information is processed by the controller, and the RF antenna is moved by a motor that advances the cable assembly along a track in the device. Such a device is suitable for use in both open and minimally invasive procedures for the creation of linear transmural lesions for the treatment of atrial fibrillation.

Another embodiment is a similar device, which contains malleable metal elements that allow the device to be formed into an arc (like a shepherd's crook) whose circumference can match the outer circumference of the base of the pulmonary vein. This device is similar in construction to the embodiment described above, except that it is attached to a rod suitable for insertion into a port access device for entry into the thorax or for manual manipulation by a surgeon in an open procedure. The device is brought into contact with the base of the pulmonary vein, and vacuum is used to attach it to a portion of the basal circumference of the vein. RF energy is delivered controllably as described above. When a full thickness lesion is created on one side of the vein, the vacuum is released, and the device moved so that its arc rests over the side of the vein that has not been treated. A full thickness lesion can then be created on that side.

For some applications, the surgeon may manually control advance of the radio frequency antenna within the template device, and control further movement with a remote control device. In particular, the surgeon can also utilize manual movement of the RF antenna assembly through a joystick or other actuation transducer that advances the RF antenna. The joystick is operated by the surgeon in response to an indicator (light, etc.) that responds to the appropriate decrease in impedance or increase in conductance time detected by the sensors mounted in the vacuum seals. As an alternative, the surgeon may simply monitor the advance of the radio frequency antenna visually, and actuate a joystick or similar device. In either case, the template device operates as both a guide and an automated actuator to translate the radio frequency antenna (or other device) along a desired path. Notably, the template device is affixed to the pertinent tissue and provides automated movement of the instrument, reducing motion problems relative to the instrument offering enhanced precision.

In one embodiment, the present invention provides a surgical device for use in a tissue ablation procedure. The device includes a contact member that engages the tissue near a location where the tissue is to be ablated. The contact member defines a guide that indicates, upon engagement of the contact member with the tissue, the location where the tissue is to be ablated, and provides a path for travel of a tissue ablation probe. The contact member of the device may include a compliant and tacky interface element for engagement with the tissue. The device may further define an interior chamber, and may include a vacuum port in fluid communication with the interior chamber. The interior chamber may be capable of delivering vacuum pressure to the contact member, thereby promoting vacuum-assisted adherence of the contact member to the tissue. In addition, the device may include a sensor that may indicate whether the desired degree of tissue ablation has been achieved.

In another embodiment, the present invention provides an apparatus for determining whether conduction paths within heart tissue have been adequately ablated during a surgical procedure. The apparatus includes a first electrode capable of transmitting a first electrical signal adjacent the tissue to be ablated, a second electrode capable of receiving a second electrical signal adjacent the tissue to be ablated and a measuring device electrically coupled to at least the second electrode to receive the second electrical signal from the second electrode. The measuring device may determine whether the extent to which the tissue has been ablated to a sufficient degree based on the second electrical signal. The apparatus further includes an output device that provides an indication of extent, e.g., depth, to which the tissue is ablated. In order to measure impedance when using RF ablation, it may be necessary to use an energy frequency outside of the ablation energy frequency range or pulse or ablation energy and measure impedance during the quiescent period between ablation pulses.

In another embodiment, the present invention provides a method for severing conduction paths within tissue. The method involves placing a first device near the target conduction paths to be severed, using the first device as a guide to sever the target conduction paths, and with a second device, measuring to determine whether the desired severing has been achieved. In this embodiment, the target conduction paths may be severed by tissue ablation. Measurement may involve determining whether the lesion depth is sufficient to sever the target conduction paths.

The details of one or more embodiments of the invention are set forth in the accompanying drawings and the description below. Other features, objects and advantages of the invention will be apparent from the description and drawings, and from the claims.

BRIEF DESCRIPTION OF THE DRAWINGS

FIG. 4 is a conceptual diagram illustrating an ablation template device in accordance with an embodiment of the invention.

FIG. 9A is a perspective top view of an ablation template device in accordance with an embodiment of the invention.

FIG. 9B is a perspective bottom view of an ablation template device as shown in FIG. 9A.

In general, like reference numerals are used to refer to like components.

DETAILED DESCRIPTION

Figure 1:
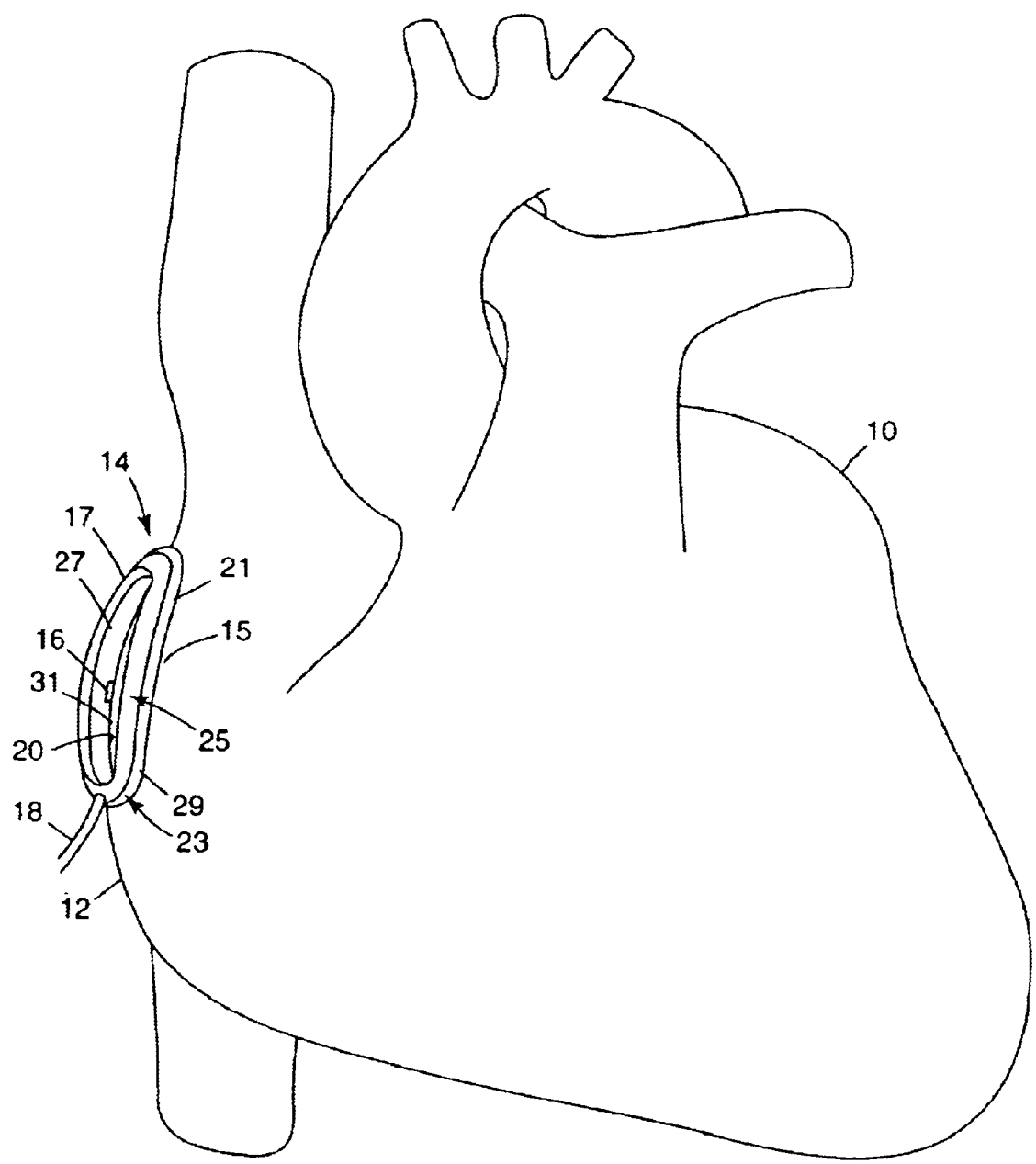
FIG. 1 is a perspective view of an ablation template device in accordance with an embodiment of the present invention placed on a heart for purposes of illustration.

FIG. 1 is a perspective view of an ablation template device 14 in accordance with an embodiment of the present invention. In FIG. 1, ablation template device 14 is shown placed on a heart 10 for purposes of illustration. In particular, heart 10 has been exposed by an open-chest surgical technique and ablation template device 14 has been affixed to the right atrium 12 of the heart. In some embodiments, ablation template device 14 includes a contact member 17 that engages the tissue. In the example of FIG. 1, contact member 17 takes the form of a substantially ovular ring. Inner and outer diameters 20, 21 of the ring-like contact member 17 define an annular chamber for engagement with tissue on the surface of heart 10.

Contact member 17 may be affixed to the surface 15 of atrium 12 in many ways, such as by application of an adhesive at the inner and outer diameters 20, 21, or by application of vacuum pressure to the annular chamber. Another way to achieve adherence between contact member 17 and the surface tissue 15 is to include a seal member 23 formed from an adhesive material in the contact member. One example of an adhesive material is a coating of compliant, tacky material, such as silicone gel, at the interface between the contact member 17 and the tissue on the surface 15 of atrium 12. In this case, contact member 17 may include a semi-rigid frame member 25 and a compliant, tacky seal member. The compliant, tacky seal member 23 provides intrinsic adhesive properties, and aids conformability and sealing to surface 15, while the frame 25 imparts structural integrity to contact member 17. Each of frame 25 and seal member 23 has a substantially annular shape. In particular, seal member 23 may include inner and outer portions 27, 29 disposed at the inner and outer diameters 20, 21 of contact member 17.

With a silicone gel, intrinsic adherence of seal member 23 may be sufficient that ablation template device 14 remains affixed to the heart 10 in spite of contractions of atrium 12 and in spite of the use of device 14 in surgical procedures described below. Nevertheless, application of vacuum pressure will be desirable in many applications to provide secure adherence. Although the adherence should be secure, the adherence preferably is not permanent. Rather, adherence between device 14 and the tissue may be discontinued as desired without serious trauma to the tissue, and the device repositioned and adhered anew at a different location. As an alternative, ablation template device 14 can be forced against atrium 12 to provide pressure contact with heart 10. In such a case, ablation template device 14 may have a local stabilizing effect on the contact region of heart 10 despite continued beating of the heart. Ablation template device 14 may be sized or shaped to allow it to mold to the contours of the atrium 12. Ablation template device 14 can be made principally of nonconductive materials, such as polyurethane, silicone, or natural or synthetic rubber. Shore A 50–80 silicone elastomer may be used, for example, to form frame 25 of device 14. Metal such as annealed stainless steel or zinc or polymeric reinforcing members may be incorporated in device 14, e.g., embedded within the molded elastomer, to resist excessive deformation or collapse during use. Shape memory alloys, in particular, may be useful in imparting a desired shape to device 14 during use, and permit collapse and unfolding to the desired position for endoscopic deployment in minimally invasive techniques.

An electrode 16 can be affixed to device 14, e.g., within seal member 23 or frame member 25, and placed in contact with the surface 15 of the heart 10. The electrode 16 may send signals across the tissue of the heart 10 to be received by a second electrode (not shown in FIG. 1). These signals will traverse the tissue area being ablated. The associated circuitry for the electrodes may reach device 14 by way of a connective tube 18. As will be described, electrode 16 may form part of a sensor for determining the effectiveness of a tissue ablation procedure. In particular, the electrodes can be used to measure electrical properties (such as impedance, phase angle, conduction time, conduction velocity, capacitance) of the local tissue area being ablated, and thereby indicate whether an effective lesion has been formed in the tissue. In some embodiments, ablation template device 14 may have multiple sets of electrodes situated at different positions along the major axis of the device. In this case, such electrodes may take the same types of measurements at different positions, or different types of measurements such as impedance, conduction velocity, and conduction time.

If ablation template device 14 is attached with the assistance of vacuum pressure, connective tube 18 may also serve the purpose of attaching the interior chamber formed by contact member 17 to an external source of vacuum pressure (not shown). Ablation template device 14 may be shaped to define an interior chamber that is enclosed upon engagement of the device with the tissue. In the example of FIG. 1, the chamber is substantially annular. Application of vacuum pressure may cause the enclosed chamber to slightly deform, creating a vacuum seal and causing the device 14 to become more affixed to the tissue. With added compliance from seal member 23, in particular, contact member 17 can conform to tissue surface 15 to achieve an effective seal. At the same time, the compliant seal member 23 distributes sealing force across the tissue to reduce tissue trauma.

As shown in FIG. 1, contact member 17 of ablation template device 14 generally may have a somewhat annular shape, with substantially oval-shaped inner and outer diameters, and an opening 31 through which the tissue of atrium 12 may be accessed. The lengths of the major and minor axes of annular-shaped device 14 may vary to provide opening 31 with varying sizes according to the characteristics of the particular procedure to be performed. In some applications, opening 31 may define a narrow, linear track for travel of an ablation probe. In other applications, opening 31 may be much wider or define nonlinear tracks for travel of an ablation probe. Other shapes for contact member 17 beside the annular shape may also be suitable.

Figure 2:
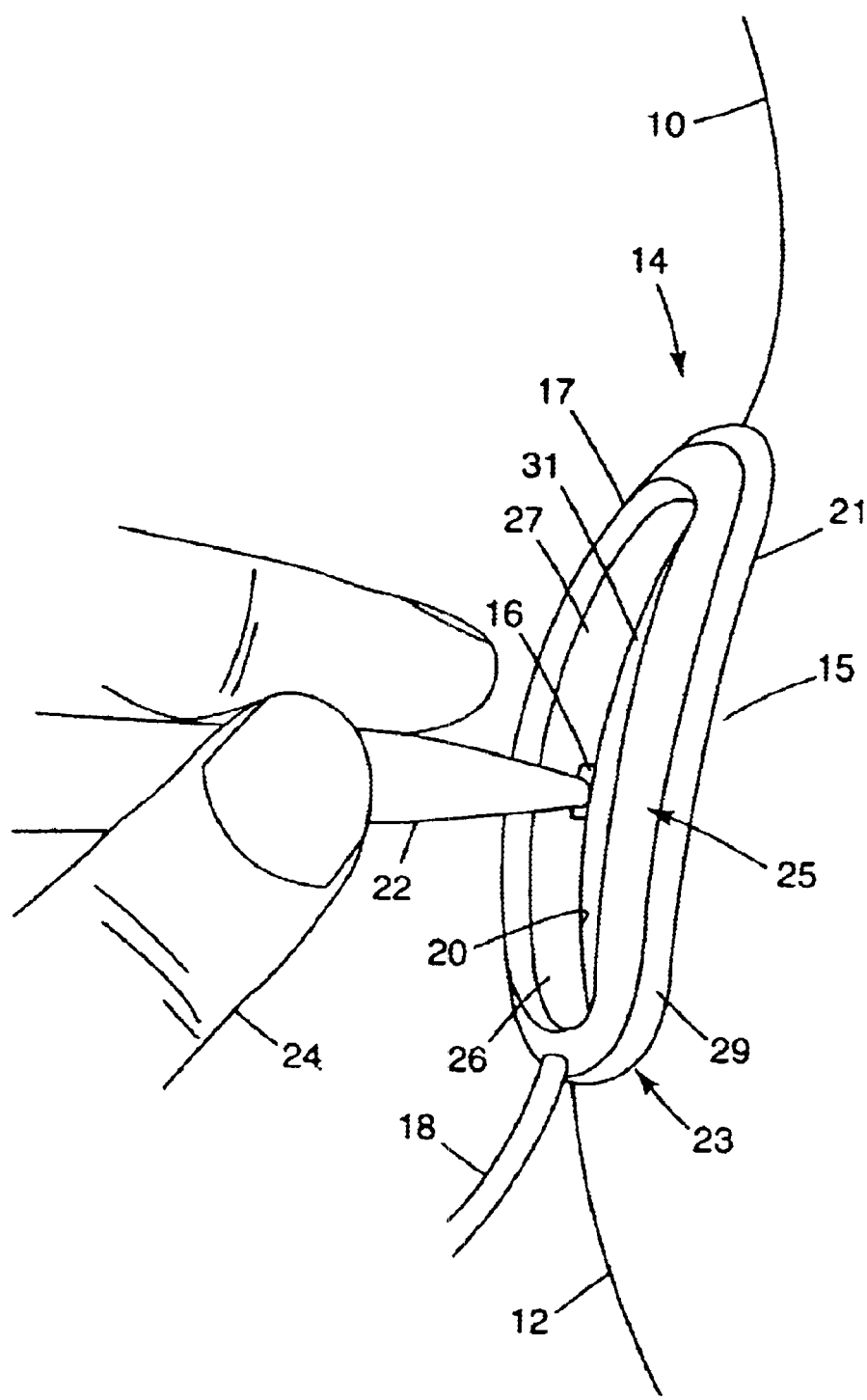
FIG. 2 is an enlarged perspective view of an ablation template device as shown in FIG. 1, showing use of a surgical instrument.

A closer perspective view of ablation template device 14 appears in FIG. 2. In FIG. 2, a surgeon's fingers 24 hold a surgical instrument shown as an ablation probe 22 that may be used to ablate the tissue of the heart 10. Even though the heart 10 is beating, the surgeon 24 may position the probe 22 within the opening 31 with relative ease. The surgeon 24 may also use the probe 22 to ablate a particular area of the atrium 12, even though the atrium 12 is in the process of contracting and relaxing, by using the inside edge 26 of the device 14 as a guide for travel of the probe. Again, opening 31 may define a substantially linear path for travel of an ablation probe. Alternatively, opening 31 can be non-linear, e.g., curved, or have other shapes appropriate for given surgical applications. In either case, the surgeon may use opening 31 as a guide, even resting the ablation probe 22 against the inside edge 26 of contact member 17 in some cases. Because significant heat may be generated by RF, laser, and ultrasonic energy, it may be desirable to provide ablation probe 22 with a thermally insulative sleeve that extends downward to the tip of the probe, thereby protecting the inside edge 26 of contact member 17. Also, inner edge 26 of contact member 17 can be coated with or coupled to an insulative material for contact with ablation probe 22.

If ablation template device 14 is fixed to a point of reference, it may provide a local stabilizing effect that holds the tissue within opening 31 substantially stationary, or at least constrains the local area against excessive movement, despite continued beating of heart 10. For example, ablation template device 14 may be pushed against heart 10 to apply stabilizing pressure to the local area of contact. Alternatively, ablation template device 14 can make use of suction or adherence in combination with either a pushing or pulling force to provide a stabilizing effect.

Ablation probe 22 may use a number of methods to achieve ablation. The probe 22 may, for example, use a laser to ablate tissue. As another alternative, the probe may incorporate an antenna that emits radio frequency (RF) energy to ablate tissue. The amount of power delivered by the ablation probe may vary. A typical RF probe, for example, may deliver from 5 to 50 watts. In this alternative, the probe 22 may include an electrode at its tip. An electrode can be provided within ablation template device 14 to provide circuit completion for a probe using RF energy. For example, a passive electrode forming part of the sensor described above could be used as the return electrode. As a further alternative, probe 22 could take the form of an ultrasound probe that emits ultrasound energy, or a cryosurgical probe that cools the tissue to ultra-low temperatures. Thermal, chemical, and mechanical probes for obtaining or incising tissue are also contemplated. In each case, opening 31 of ablation template device 14 provides a guide for travel of probe 22, enabling greater precision in the ablation of conduction paths within the heart tissue.

Figure 3A:
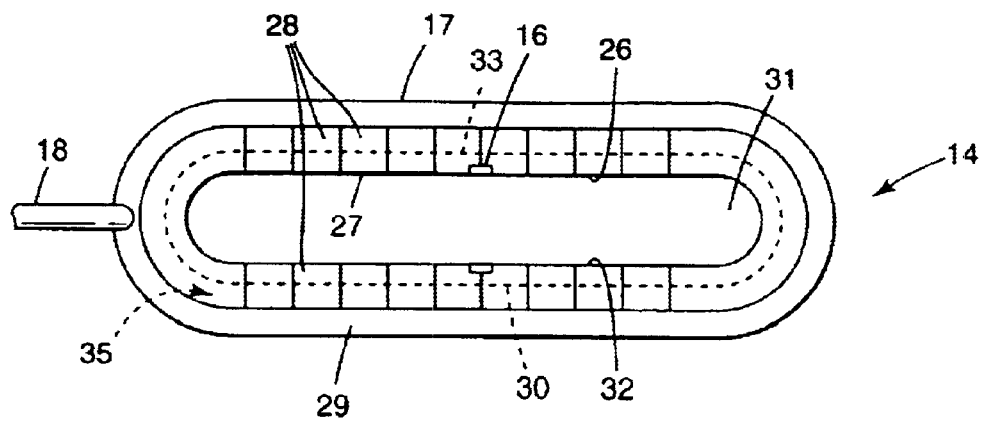
FIG. 3A is a top view of an ablation template device in accordance with an embodiment of the invention.
Figure 3B:
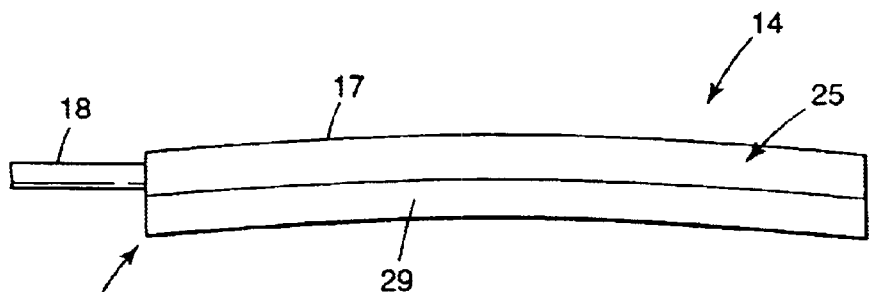
FIG. 3B is a side view of an ablation template device in accordance with an embodiment of the invention.
Figure 3C:
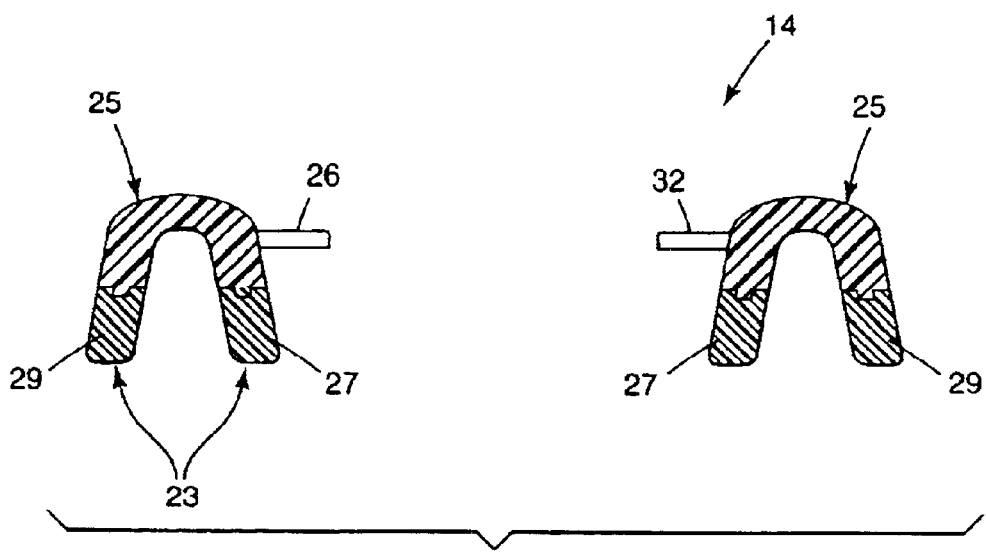
FIG. 3C is a cross-sectional side view of the device of FIGS. 3A and 3B.

Other views of ablation template device 14 appear in FIGS. 3A and 3B. In these views, the device is shown in a top view, FIG. 3A, and a side view, FIG. 3B. FIG. 3C is a cross-sectional side view of the device of FIGS. 3A and 3B. Inner seal member 27 is indicated by dashed line 33. The interior chamber of contact member 17 is indicated by reference numeral 35. Ablation template device 14 may be flexible, and its relaxed shape may be curved as shown in FIG. 3B to more readily conform to the surface of the heart. The exemplary annular shape allows first electrode 16 and second electrode 30 to be located opposite to each other across the opening 31. The distance between the electrodes 16, 30 may be a known, fixed distance. The interior edges 26, 32 of the opening 31 preferably have sufficient rigidity to serve as a guide for travel of a probe or other surgical instrument. Although seal member 23 may be substantially compliant and conformable, the inner edge of frame member 25 may provide the degree of rigidity desirable to support the probe. In addition, ablation template device 14 may include one or several length indicators in the form of visible markings 28, to assist the surgeon in forming a lesion of a desired length.

A surgeon desiring to make a lesion of a particular length may use the markings 28 as a guide for manipulating the probe. Thus, the guide provided by opening 31 is useful in guiding both the direction of travel of the probe and the extent of travel. Also, the template device 14 may include a structure that physically restricts the length of travel of the ablation probe, as well as the shape of the path along which the probe travels. Substantially straight ablation tracks ordinarily will be desirable. Accordingly, the guide surface on the interior of the opening may be substantially straight. In other applications, however, it may be desirable to effect a curved ablation track. Therefore, the shape of the guide within opening 31 may vary according to the application. Furthermore, because ablation typically causes a change in tissue color, the markings 28 may provide the surgeon with information as to the actual length of the lesion.

In one aspect, the invention can be useful in determining whether the conduction path has indeed been cut. Ordinarily, a surgeon cannot visually gauge the depth of a lesion. The guide defined by ablation template device 14 may provide an indication of the length of a lesion. A lesion of an insufficient depth may result in currents that pass under or over the lesion, however, and may thus be incapable of disrupting the reentry circuits or other undesirable current pathways. The myocardium consists of interlaced bundles of cardiac muscle fibers. Within the fibers, cardiac muscle cells are joined by intercalated discs, which include areas of low electrical resistance known as gap junctions. Gap junctions permit excitations or action potentials to propagate from one cell to another. A lesion created by ablation may destroy the tissue and the gap junctions, effectively interrupting electrical conduction. Thus, determination of whether the conduction paths are indeed ablated may be crucial to a successful treatment.

As shown in FIGS. 3A and 3B, ablation template device 14 may include at least two electrodes, 16, 30 that operate as part of a sensor. A sensor may be used to indicate to the surgeon whether a desired degree of tissue ablation has been achieved. Electrodes 16, 30 preferably are integrated with ablation template device 14 to reduce the number of instruments that need to be introduced in to the surgical field. In particular, electrodes 16, 30 can be molded into the material forming seal member 23 or frame member 25, and have conducting members that extend away from the tissue site via tube 18. A tip portion of each electrode may be exposed beyond the surface of seal member 23 to enable sufficient electrical contact with the tissue to which contact member 17 is attached.

In other embodiments, however, electrodes 16, 30 may be introduced independently of ablation template device 14. FIGS. 3A and 3B show an exemplary embodiment of the present invention, and other embodiments may incorporate more than two electrodes. After an ablation is performed inside the opening 31, and during ablation, electrodes 16 and 30 may be located on opposite sides of the lesion. The distance between electrodes 16 and 30 may be a known distance and relatively fixed. The electrodes 16, 30 may be used to determine whether the conduction path has been severed by ablation to the desired degree.

One way to make the determination is to use the electrodes 16, 30 as probes for an impedance-measuring instrument. Electrodes 16, 30 may be electrically coupled to the impedance-measuring instrument. The impedance of the area of tissue may be measured before any ablation is made, and this measurement may be used as a baseline. The impedance may be measured again after the ablation is made and may be compared with the baseline measurement to determine whether the conduction path has been severed. Moreover, it may be desirable to measure impedance during an ablation procedure to assess progress in producing an effective lesion. During ablation, impedance measured from one side of the lesion to the other side will decrease as ablation ruptures cell membranes, permitting dissolved ions to move with less restriction. Impedance will generally decrease until impedance reaches a minimum value when the lesion becomes transmural. One way to determine whether the ablation is complete is to look for the point at which the impedance measurement levels off. For example, a baseline measurement on canine atrial myocardium may show an impedance of 240 ohms, but measurements taken during the ablation may show a steady decline in impedance, eventually leveling off at 150 ohms after about 90 seconds. It may also be possible in some circumstances to evaluate the ablation process on the basis of a percentage change of impedance or on the basis that a predetermined impedance value has been reached. Parameters such as the baseline value, the leveling off value and the time needed to produce a transmural lesion are dependent upon the patient being treated, the tissue being ablated, the distance of the electrodes, the thickness of the tissue, and other factors. In the case of the heart, for example, not all hearts have the same impedance, and different sections of a single heart may also have varying impedance. In such cases a baseline measurement may be desirable, with transmural penetration indicated by the leveling off of impedance measurements.

In addition to measuring impedance or as an alternative to measuring impedance, alternating current (ac) phase angle may be measured. In a capacitive circuit, the voltage lags the current, and the amount of lag is often expressed in the form of a phase angle. In a purely capacitive circuit, the voltage is 90° behind the current, expressed as a phase angle of −90°. A phase angle of 0° means the circuit is purely resistive. A phase angle between 0° and −90° means the circuit is partly resistive and partly capacitive. Typically a phase angle measurement across tissue will be between 0° and −90°, indicating some capacitive nature of the tissue. As ablation proceeds, cell membranes are ruptured, making the tissue less capacitive. Accordingly, the phase angle across the ablative lesion will become more positive (i.e., will approach zero) as cells die in the lesion. One way to determine whether the ablation is complete is to look for the point at which the phase angle measurement levels off. A baseline measurement of canine myocardium, for example, may show a phase angle of −13.1°. Measurements taken during the ablation may show the phase angle becoming more positive, eventually leveling off at −12° after about 20 seconds. As with impedance measurements, phase angle measurements are dependent upon many factors.

Another way to make the determination is to use the electrodes to measure conduction distance by measuring conduction time. A signal traveling on a conduction path propagates as an action potential and propagates via gap junctions. The length of a conduction path, the speed of conduction and the time taken for a signal to travel the path are related by the simple formula $$D=RT$$

where D is the distance traveled by the signal, R is the rate of speed of the signal, and T is the time taken for the signal to travel the distance. In the case of an actual operation, a particular value of D or T may be desired. A value for R may be obtained by sending a test signal from one electrode, receiving it at the other electrode, the distance between the electrodes being known and relatively fixed, and measuring the time of conduction. In many cases, however, a relative measure of conductive velocity or time is sufficient, and therefore the distance between electrodes need not be known absolutely so long as it remains fixed. This measurement may then be used as a baseline measurement. Again, a baseline measurement may be desirable, because not all hearts have the same conduction speed, and different sections of a single heart may also have varying conduction speeds. The time of conduction may be measured again after the ablation is made and may be compared with the desired value of D or T. In general, conduction time increases and conduction velocity decreases as the ablation proceeds, and one way to determine whether the ablation is complete is to look for the point at which the measured quantity levels off. For example, a conduction time of 15 ms may be measured as a baseline. During ablation, conduction time may increase, eventually leveling off at around 30 ms. The leveling off indicates the ablation is transmural.

In the case of measurement of conduction time, velocity, or distance, electrode 30 may be a single electrode or a bipolar or multipolar electrode. Thus, in the description of this invention, it is to be understood that the transmitting electrode 16 positioned on one side of the ablation track may be unipolar, while the measurement or "recording" electrode 30 positioned on the opposite side of the ablation track can be unipolar, bipolar, or multipolar, depending upon the electrical measurement that is utilized to determine if the conduction paths have been severed or ablation of the target tissue has been transmural, and desired precision. With a unipolar recording electrode 16, an electrical signal transmitted into the tissue by the transmitting electrode is first sensed as an electrical signal that is then followed by a depolarization wavefront that propagates through the cells disposed between electrodes 16, 30. It is the depolarization wavefront that is detected to measure conduction time. unipolar recording electrode 30 simply measures whether the depolarization wavefront exceeds a given threshold. With a bipolar recording electrode 30, however, the two electrodes can be used to measure current flow or a voltage potential between them. The two electrodes of the bipolar recording electrode 30 can be oriented in a line substantially parallel to the ablation track, and thereby form a "T" with the transmitting electrode 16. As the depolarization wavefront propagates through the cells positioned between transmitting electrode 16 and recording electrode 30, the cells disposed between two recording electrodes of bipolar recording electrode 30 depolarize, producing a difference in current flow between the two recording electrodes. This bipolar arrangement enables measurement of an increase in the intensity of current flow between the two electrodes of bipolar recording electrode 30, and more precision in the measurement. In particular, an intensity threshold can be set. Conduction time can be measured between the time at which transmitting electrode 16 transmits the initial signal and the time at which current flow between the two electrodes of bipolar recording electrode 30 exceeds the threshold. Again, the initial signal transmitted by, transmitting electrode 16 and sensed by the recording electrode 30 can be ignored. Rather, the depolarization wavefront typically will be the event of interest in determining conduction time.

A method of using measurement of impedance or conductance variables to determine the transmurality of a lesion may also be employed using bipolar radio frequency electrosurgical ablation devices. For example, separate electrodes, using an electrical frequency different from the frequency used by the ablation device, can be mounted on the device and used to form a separate measuring circuit for impedance for the purpose of measuring the distance ablated. A typical bipolar device could have two electrode surfaces, one for one side of a tissue surface and one for the other side of a planar tissue surface, such as the myocardium, or a vascular structure. One transmitting electrode, or a plurality of electrodes, can be mounted with one of the surgical electrodes, and a receiving or "recording" electrode, which could be bipolar or multipolar, or a plurality of unipolar, bipolar, or multipolar electrodes, can be mounted on the opposite surgical electrode. Impedance or conductance, such as time, distance, or velocity, can be measured as described herein and can be used to determine transmurality, and shut off power to the ablation device as described. It is envisioned that one specific application of such a bipolar device would be for deployment through a puncture hole in the myocardium. The ablation device could be equipped with "jaws" that carry the electrodes. Entry of one of the "jaws" of the surgical RF device could be either from the endocardial or epicardial surfaces. After deployment, there would be a surgical electrode on both the epicardial surface and the endocardial surface. As RF power is supplied to the surgical ablation device, the tissue between the two surgical electrodes is heated and killed, creating a lesion for the purpose of interrupting conductance pathways. The transmurality of this lesion at different points along its length can be measured simultaneously or at time intervals during ablation using measurement of impedance or conductance variables with the separate circuits defined by the transmitting and recording electrodes placed along the path of the surgical electrodes and the underlying lesion.

FIG. 4 shows a conceptual diagram of an implementation of an aspect of the invention. Electrodes 16, 30 shown in FIG. 3 may serve as probes 34 for a measurement device 36. The measurement device 36 may measure a quantity related to conduction, such as impedance or conduction time or conduction velocity. Data measured by measurement device 36 may be fed into a processor 38. Processor 38 may be in the form of a generalized computing device, such as a personal computer. Alternatively, processor 38 may be in the form of a smaller and more specialized computing device, such as a microprocessor or an application-specific integrated circuit. As a further alternative, processor 38 could be realized by discrete logic circuitry-configured appropriately to perform the necessary measurement control and processing functions. Accordingly, processor 38 need not be embodied by integrated circuitry, so long as it capable of functioning as described herein.

In addition, processor 38 may take an active role in the measurement process and may control measurements made by measurement device 36 through probes 34. In particular, processor 38 may control a current or voltage source to apply electrical current or voltage to one of electrodes 16, 30. Two representative instances where the processor 38 may actively control the measurement process are in the taking of a baseline measurement, and in the taking of periodic measurements during the ablation procedure to monitor progress. Processor 38 may further perform calculations as needed, and may provide output to the surgeon by way of an output device 40 such as a display. In addition, processor 38 may receive input from an additional input device 42, which may include, for example, a keyboard or a touch screen. Using input device 42, the surgeon may, for example, input the length of a desired lesion, and the processor 38 may be able to provide feedback to the surgeon via output device 40 as to whether the desired lesion has been created. Output device 40 may provide audible and/or visible output such as beeps, flashing light emitting diodes (LED's), speech output, display graphics, and the like, to provide feedback to the surgeon. Output device 40 can be mounted in a housing associated with processor 38, or integrated with the ablation probe 22. For example, one or more LED's could be mounted on the ablation probe in view of the surgeon.

Figure 5:
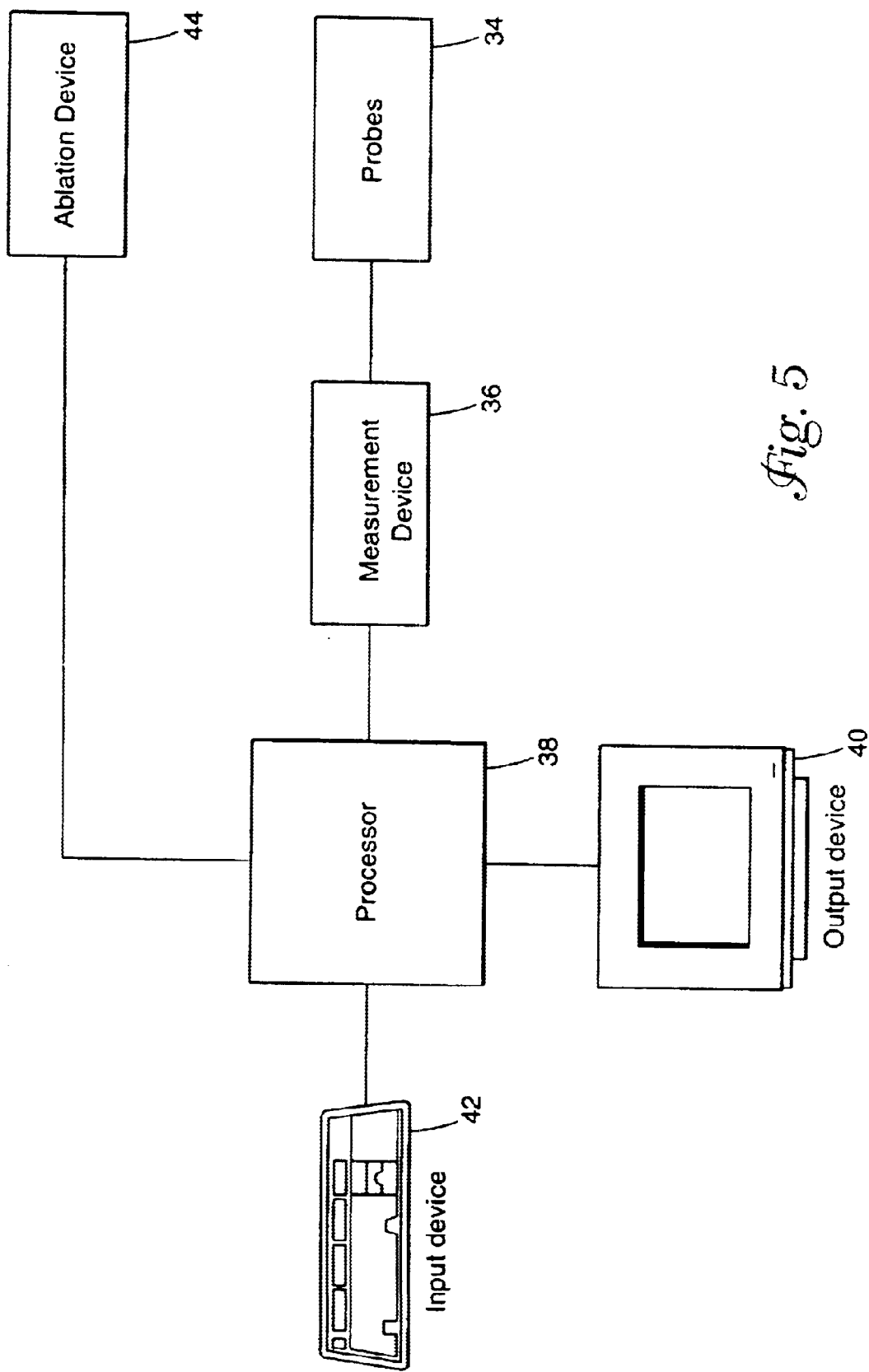
FIG. 5 is another conceptual diagram illustrating an ablation template device in accordance with an embodiment of the invention.

FIG. 5 shows another conceptual block diagram of an implementation of an aspect of the invention. FIG. 5 is similar to FIG. 4, except that the processor 38 is connected to the ablation device 44. Ablation device 44 may be any device intended to sever conduction paths by killing tissue, such as the RF, laser, ultrasonic, or cryogenic probe 22 depicted in FIG. 2. In each case, ablation device 44 may be in the form of a powered instrument such as a laser, RF, or ultrasonic electrosurgical probe, or be coupled to a cryogenic supply. Processor 38 may control ablation device 44 by, for example, cutting off power or supply to the ablation device once the desired lesion has been created. In this manner, the surgeon can take advantage of closed-loop, real-time control of the output of ablation device 44, ensuring ablation to a proper level of effectiveness and avoiding excessive ablation. The result may be the creation of an effective lesion in a shorter time period, reducing the time necessary for access to,the patient's heart tissue. The system may be even more effective if multiple electrode pairs are mounted along opening 31 to measure the effectiveness of ablation in creating a lesion along a continuous track.

The system shown in FIG. 5 may be useful for dynamic monitoring and control of the surgical procedure. The surgeon may choose an ablation device 44, such as a laser, that will not interfere with the operation of the probes 34. Alternatively, if interference is created by an RF probe, power can be intermittently turned off to enable measurement. By any combination of taking a baseline measurement or receiving input through input device 42, the processor 38 may determine what measurements received from measurement device 36 will satisfy the conditions for a successful surgical procedure. Processor 38 may continuously or frequently monitor the measurements received from measurement device 36 to determine whether the criteria for a successful surgical procedure have been met. When those criteria have been met, processor 38 may cut off power to, or otherwise interrupt the operation of, ablation device 44. In other words, processor 38 may use a feedback system as part of its control of ablation device 44 for either automated control or manual control by the surgeon.

One advantage of this system is the speed by which the surgeon may perform the ablation procedure. Speed is of a considerable advantage to the patient in several respects. First, risks attendant to surgery may be minimized if the time spent on the operating table is reduced. Second, a procedure performed on moving tissue such as a beating heart may be more efficient if done quickly.

Figure 6:
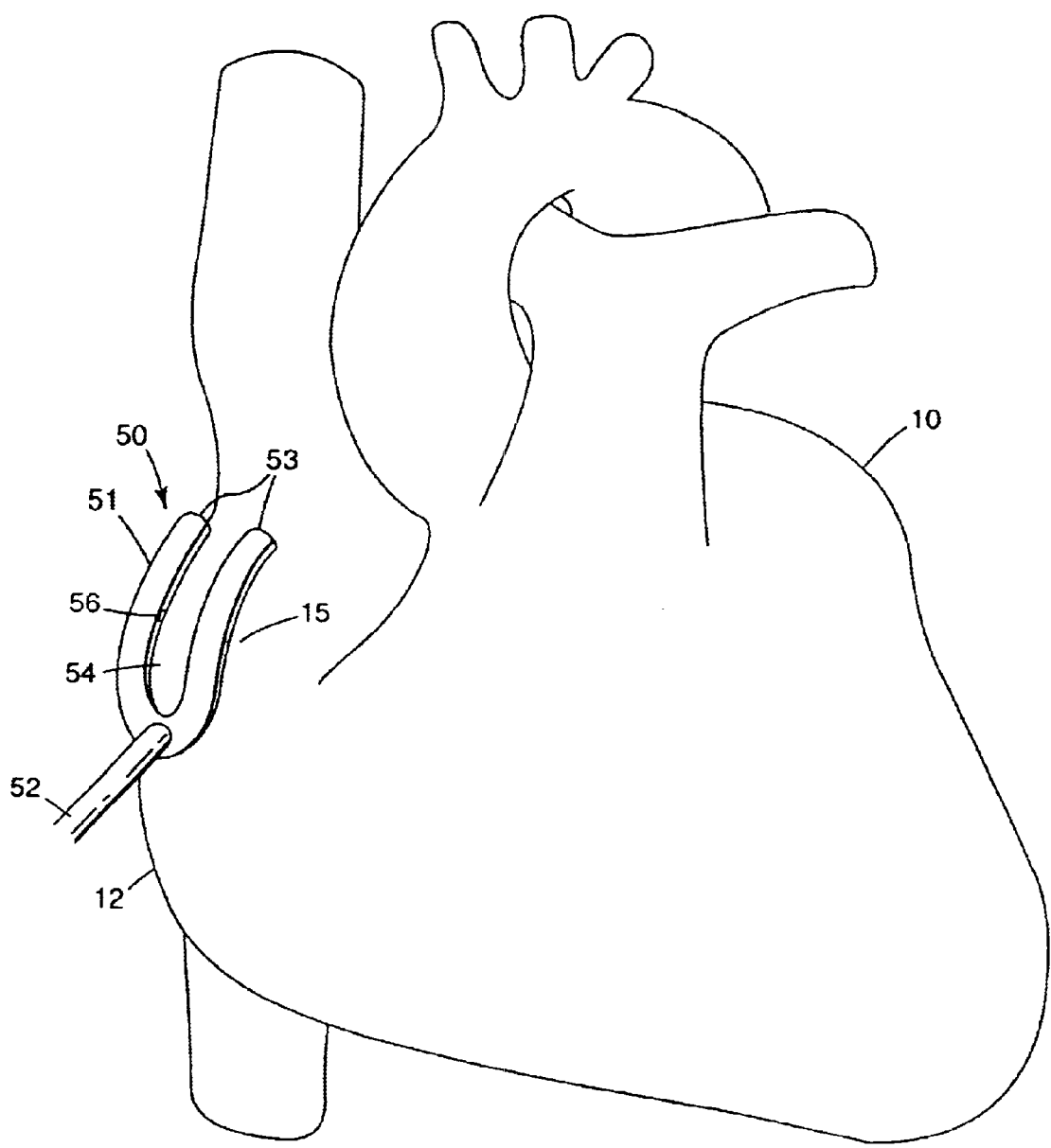
FIG. 6 is a perspective view of an ablation template device in accordance with an alternative embodiment of the invention placed on a heart for purposes of illustration.

Once ablation template device 14 is placed into position, a baseline measurement may be taken, and the surgeon may then proceed to make the ablation, using ablation template device 14 as a template or a guide. Use of the device 14 as a template or guide is one factor enhancing the speed of the procedure. The surgeon may use markings 28 on ablation template device 14 to get a general idea of where to begin and end the ablation. The processor 38 may be used to suggest to the surgeon via output device 40 suitable markings 28 for beginning and ending the ablation pass. The surgeon may then make a pass with the ablation device 44. If the pass is too long, the processor 38 may interrupt the function of the ablation device 44 before the pass is completed. If the pass is too short, the processor 38 may assist the surgeon in determining the best approach for a second pass. Again, the length determination may be aided by the use of a series of electrode pairs along an ablation track. The use of dynamic processing and feedback further enhance the speed of the procedure. FIG. 6 is a perspective view of an ablation template device 50 in accordance with an alternative embodiment of the present invention. Like ablation template device 14 in FIG. 1, ablation template device 50 is shown placed on the right atrium 12 of a heart 10 in FIG. 6 for purposes of illustration. In particular, heart 10 has been exposed and ablation template device 50 has been affixed to the right atrium 12 of the heart. Ablation template device 50 includes a contact member 51 which may engage and may be affixed to the surface 15 of atrium 12 by being pushed against the heart. Because ablation template device 50 generally has a U-shaped shape, contact member 51 includes two contact tines or contact "feet" 53.

Electrodes used to take the measurements described herein may take the form of discrete electrodes that operate in pairs to transmit and receive signals across the ablated tissue region. Alternatively, one or more of the electrodes may take the form of bipolar or electrodes that are integrated in a common electrode package and positioned in very close proximity to one another. With the closer spacing available in a bipolar package, for example, the signal transmitted by one electrode and received by the other as an EMG potential can be cleaner in terms of having a reduced degree of background noise due to surrounding electrical potentials produced by the heart. Instead, the bipolar electrode is capable of more effectively measuring the local signal conduction time. Also, in some embodiments, series of electrodes on each side of the ablation track can be realized by a continuous electrode component that includes conductive electrode regions and insulating regions disposed therebetween. Again, this sort of component can permit closer electrode spacing. In this case, however, the closer spacing is not between transmitting and receiving electrodes but between adjacent transmitting electrodes and adjacent receiving electrodes extending parallel to the ablation track. The closer spacing permits a higher degree of resolution in monitoring the progress of the ablation procedure along the ablation track, and thus the length of the resulting lesion. The closer spacing permits more precise feedback and control of the ablation probe by the surgeon or by an automated controller.

To maintain its position relative to the heart 10, ablation template device 50 may, in addition, have a compliant, tacky material such as silicone gel at the point of contact between contact member 51 and the surface 15 of the atrium 12, providing a compliant, tacky interface. Ablation template device 50 may remain substantially affixed to the heart 10 in spite of contractions of atrium 12 and in spite of the use of ablation template device 50 in surgical procedures described such as those described above. By being forced against the heart, ablation template device 50 may have a stabilizing effect on the contact region of heart 10 despite continued beating of the heart. Shaft 52, made of a rigid material and formed in any suitable shape, may be used to press ablation template device 50 against atrium 12 and hold the device in place.

Although ablation template device 50 may be more rigid than ablation template device 14 in FIG. 1, ablation template device 50 may be sized or shaped to allow it to mold to the contours of the atrium 12. Like ablation template device 14 in FIG. 1, ablation template device 50 can be made (with the exception of the compliant, tacky interface) principally of substantially rigid, nonconductive materials, and may include a first electrode 56 and a second electrode (not shown in FIG. 6). The associated circuitry for the electrodes may reach ablation template device 50 by way of shaft 52. The general U-shape of ablation template device 50 includes an opening 54 through which the tissue of atrium 12 is accessible. The dimensions of ablation template device 50 and opening 54 may vary. Other shapes beside the U-shape may also be suitable for the device 50, such as the annular shape, and the opening 54 may be in other suitable shapes as well.

Figure 7:
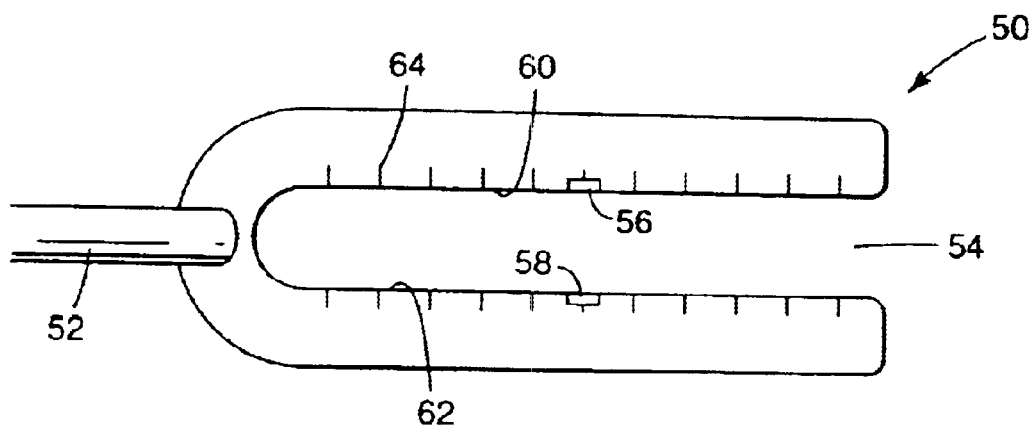
FIG. 7 is a top view of an ablation template device in accordance with an embodiment of the invention.

A top view of ablation template device 50 appears in FIG. 7. The exemplary U-shape allows first electrode 56 and second electrode 58 to be located opposite to each other across the opening 54. The distance between the electrodes 56, 58 may be a known, fixed distance. The interior edges 60, 62 of the opening 54 have sufficient rigidity to serve as a guide for travel of a probe or other surgical instrument. In addition, like ablation template device 14, ablation template device 50 may include several length indicators 64, to assist the surgeon in forming a lesion of a desired length.

Figure 8:
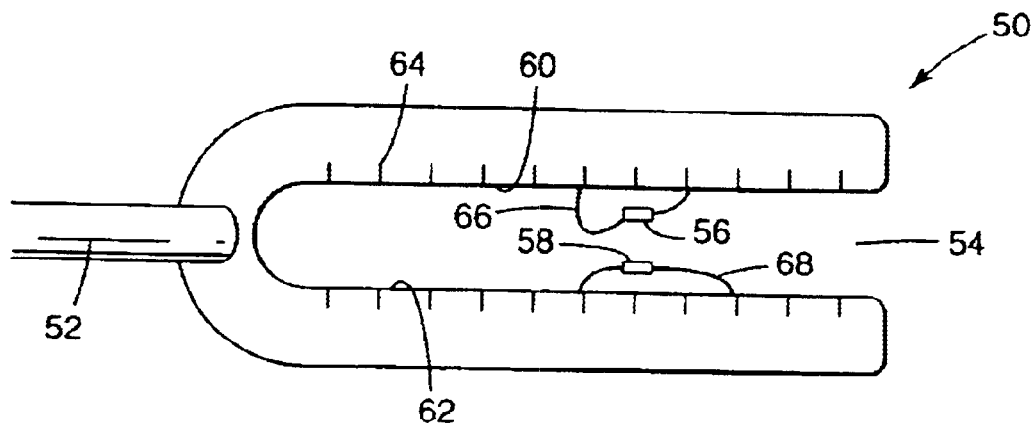
FIG. 8 is a top view of an ablation template device in accordance with an embodiment of the invention.

A top view of a variation of ablation template device 50 appears in FIG. 8. Ablation template device 50 is like the same device depicted in FIG. 7, except the first electrode 56 and second electrode 58 are not rigidly affixed to the body of the device 50. Electrodes 56, 58 are electrically coupled to ablation template device 50 by way of electrical connectors 66, 68. Electrical connectors 66, 68 may be flexible wires, and may allow a surgeon to place electrodes 56, 58 at a desired location on the tissue or at a desired distance apart.

Alternatively, electrical connectors 66, 68 may be spring-like connectors, that may appear somewhat like insect antennae, and which may force the electrodes 56, 58 against the tissue when the ablation template device 50 is pressed against the tissue to enhance electrical coupling pressure and surface area. As shown in FIG. 8, electrodes 56, 58 may be deployed within the opening 54. Electrodes 56, 58 may also be deployed at other locations as well.

FIGS. 9A and 9B show an ablation template device 69, which is similar to the ablation template device 14 shown in FIG. 1. However, FIGS. 9A and 9B illustrates a frame member 75 and a seal member 77 in somewhat greater detail. FIG. 9A is a perspective top view of device 69, while FIG. 9B is a perspective bottom view of device 69. FIGS. 9A and 9B differ slightly in the shape of device 69. Specifically, device 69 of FIG. 9A is shown as having a somewhat curved contour for conformability to the surface of the tissue.

Frame member 75 can be formed from a semi-rigid material that lends structural integrity to contact member 73, while seal member 77 is formed from a more compliant material that facilitates conformance of the contact member to the tissue surface and promotes a seal that is generally atraumatic and more effective. Seal member 77 includes an inner skirt-like member 70 coupled to and extending around the inner edge of contact member 73 that acts as an interface with the tissue. Skirt-like member 70 may function in part as a seal gasket. Ablation template device 69 also includes an outer skirt-like member 72, coupled to and extending around the outer edge of the contact member 73. Skirt-like members 70, 72 define annular vacuum chamber 76. Inside of skirt-like member 70, contact member 73 defines opening 81 for access to a tissue site. Skirt-like members 70, 72 may be composed of a material that is generally more compliant and conformable than the rest of contact member 73.

Use of Shore A 5–10 durometer silicone elastomer for the skirt-like member 70, 72 may be appropriate for some applications. Silicone gels are preferred, however, due to the intrinsic compliance and tackiness provided by such materials. Like silicone elastomers, silicone gels can be manufactured with a range of crosslink densities. Silicone gels, however, do not contain reinforcing filler and therefore have a much higher degree of malleability and conformability to desired surfaces. As a result, the compliance and tackiness of silicone gel materials can be exploited in skirt-like members 70, 72 to provide a more effective seal. An example of one suitable silicone gel material is MED 6340, commercially available from NUSIL Silicone Technologies, of Carpinteria, Calif. The MED 6340 silicone gel is tacky and exhibits a penetration characteristic such that a 19.5 gram shaft with a 6.35 mm diameter has been observed to penetrate the gel approximately 5 mm in approximately 5 seconds. This penetration characteristic is not a requirement, but merely representative of that exhibited by the commercially available MED 6340 material.

Metal or polymeric reinforcing tabs can be incorporated in skirt-like members 70, 72 to prevent collapse, and promote structural integrity for a robust seal. Skirt-like members 70, 72 can be compliant, tacky silicone gel molded about the reinforcing tabs. In particular, for manufacture, frame member 75 can be molded about reinforcing tabs or springs, allowing a portion of the tabs or springs to extend downward, to one or both of the inner diameter or outer diameter side of the annular contact member. Then, one or both skirt-like members 70, 72 can be molded onto frame member 75, encasing the exposed portions of the tabs or springs. In the example of FIG. 9, outer skirt-like member 72 and the outer diameter side of member 75 are molded about and encase a continuous spring member, shown partially in FIG. 9 and indicated by reference numeral 79. Spring member 79 can be shaped from a continuous length or one or more segments of spring steel, or other materials capable of exerting a spring bias on contact member 73.

When ablation template device 69 is placed in contact with tissue, skirt-like members 70, 72 may promote adherence between the tissue and the device. Furthermore, ablation template device 69 may include a vacuum port 74. When vacuum pressure is supplied by connective tube 71 to vacuum port 74, skirt-like members 70, 72 may promote the creation of a seal, further enhancing the adherence of device 69 to the tissue. Upon application of vacuum pressure, skirt-like members 70, 72 may deform slightly, conforming to the surface of the tissue and helping define a sealed vacuum chamber 76 having a substantially annular shape. Skirt-like members 70, 72 may therefore improve adherence to the tissue in two ways: by being tacky and compliant, and by assisting the creation of a vacuum seal. Silicone gels, such as NuSil 6340, may be especially well suited for this function, providing a quality of adherence and compressibility appropriate for the intended purposes.

Figure 10:
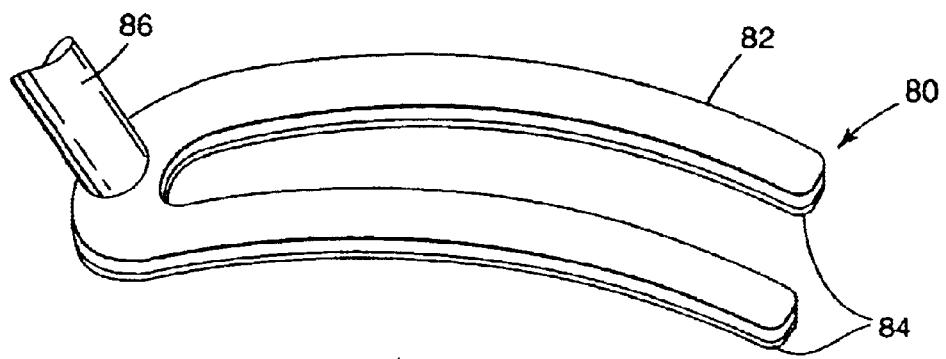
FIG. 10 is a perspective view of an ablation template device in accordance with an embodiment of the invention.

FIG. 10 shows a perspective view of an ablation template device 80, which is similar to ablation template device 50 shown in FIG. 6. The contact member 82 of the device 80 has been supplied with a thin layer of a compliant, tacky substance 84 such as a silicone gel. When ablation template device 80 is held by pressure against tissue using shaft 86, tacky layer 84 may provide added adherence between the device and the tissue, and may reduce the risk of slippage. The tacky material may be included at every point of contact between the tissue and contact member 82, or at selected sites of contact.

Figure 11:
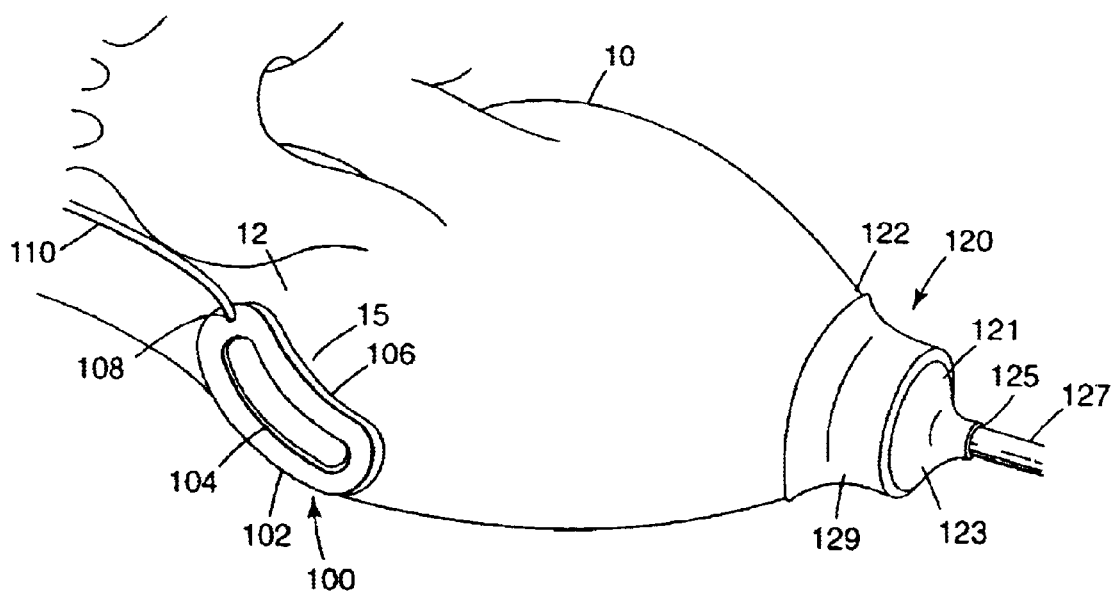
FIG. 11 is a perspective view of an ablation template device in accordance with an embodiment of the present invention, placed on a heart for purposes of illustration, used in cooperation with another device that permits manipulation of the heart.

FIG. 11 is a perspective view of an ablation template device 100, shown placed on a heart 10 for purposes of illustration. Ablation template device 100 is like ablation template device 69 shown in FIG. 9. Contact member 102 has been placed against the surface 15 of the right atrium 12. Inner skirt-like member 104, extending around the inner edge of contact member 102, and outer skirt-like member 106, extending around the outer edge of contact member 102, assist in substantially affixing device 100 to the heart 10. Vacuum pressure supplied to vacuum port 108 via connecting tube 10 may promote additional adherence between contact member 102 and heart surface 15.

It may be difficult for a surgeon to obtain direct access to the tissue of the atrium 12 where ablation is to be performed. It may be necessary for the surgeon to manipulate or move the heart so that access may be obtained. FIG. 11 illustrates the use of a surgical manipulating device 120, whereby the apex 122 of the heart 10 is held and manipulated, allowing the surgeon to obtain access to the desired site on the atrium 12. It is known that some significant portion of the aberrant impulses responsible for atrial fibrillation can originate in myocardial cells that have migrated to the inner base of the pulmonary veins. Accordingly, it is important that ablation lines be drawn in such a way as to isolate the pulmonary veins and prevent those impulses from traveling into the atrial tissue. Accomplishing this isolation requires that the ablation lines be drawn relatively close to the base of the pulmonary veins.

The use of surgical manipulating device 120 and similar devices described herein enables the surgeon to grasp the apex 122 of the beating or stopped heart 10 and access the base of the pulmonary veins, e.g., by lifting, pulling, and/or turning the beating heart to expose the pulmonary veins. Important additional benefits of device 120 and similar devices described herein may include the ability to lift and manipulate the heart 10 without causing significant trauma to the epicardium and with minimal or no disturbance of hemodynamics, reducing the overall risk of the procedure to the patient. The rigid handle 127 on device 120 permits the surgeon to apply axial (i.e., along axis from top of heart to apex) tension to the beating heart while lifting the heart 10 from the pericardial cavity. Maintaining axial tension while lifting the heart from the supine position to a position 90–110 degrees from the spine prevents distortion of valves and the decline in cardiac output that occurs when the heart is lifted by the surgeon's hand alone.

In some embodiments, two suction devices, e.g., like surgical manipulating device 120, can be used to access the posterior of the heart and the base of the pulmonary veins. One device may be applied to the apex of the heart and the second device may be applied to a suitable location on the anterior surface of the heart, such as the area between the right and left ventricles (interventricular groove). Both devices can then be manually manipulated in concert so that the heart can be raised to a vertical position, i.e., close to 90 degrees from its ordinary anatomic orientation, without distorting the axis that runs from the apex to the great vessels. In addition, manual manipulation of both devices simultaneously permits the surgeon to move the raised heart from left to right inside the thoracic cavity. The use of the second device on the anterior surface of the heart keeps the chambers and valves in the heart from being compressed or distorted, and permits elevation and rotation of the heart without compromising blood flow. No decline in blood pressure (measured just below the aortic arch with an intravascular transducer) is observed when these manipulations are performed with the two devices used in concert. The two devices (each of which may conform substantially to device 120) can also be secured by a suitable clamp or frame that is anchored to the operating table or the chest retractor.

Manipulating device 120, as shown in FIG. 11, may define a cup-like chamber 123 having a vacuum port 125 coupled to a vacuum tube 127. Chamber 123 can be formed from a cup frame 121 formed with semi-rigid material and a compliant, tacky skirt-like member 129. Vacuum tube 127 may be coupled to an external vacuum source for delivery of vacuum pressure to the interior of chamber 123.

Compliant, tacky skirt-like member 129 can be formed, for example, from silicone gel, and can be attached to an outer wall defined by chamber 123 to provide a sealing interface with tissue at apex 122 of heart 10. Skirt member 129 can be molded, cast, deposited or otherwise formed about the wall of chamber 123, or adhesively bonded to the chamber wall. Although the tackiness of skirt member 129 promotes adherence, adherence may be improved by application of the vacuum pressure via tube 127 and port 125. Upon application of vacuum pressure, at least a portion of the seal member 129 deforms and substantially forms a seal against the surface. Device 120, in various embodiments, may correspond substantially to similar devices described in the U.S. provisional application serial No. 60/181,925, filed Feb. 11, 2000, to Sharrow et al., entitled "DEVICES AND METHODS FOR MANIPULATION OF ORGAN TISSUE," and bearing attorney docket no. 11031-004P01, the entire content of which is incorporated herein by reference.

The semi-rigid chamber 123 imparts structural integrity to the device 120, while the tacky, deformable material forming the skirt-like member 129 provides a seal interface with the heart tissue that is both adherent and adaptive to the contour of the heart. Moreover, as the skirt-like member 129 deforms, it produces an increased surface area for contact with the heart tissue. The increased surface area provides a greater overall contact area for adherence, and distributes the coupling force of the vacuum pressure over a larger tissue area to reduce tissue trauma. In general, the structure of device 120 can be helpful in avoiding ischemia, hematoma or other trauma to the heart 10. Device 120 provides a grasping point, however, for manipulation of heart 10 to provide better access to a desired surgical site, e.g., by lifting, turning, pulling, pushing, and the like. Once the desired presentation of heart 10 is achieved using device 120, the heart can be held relatively stationary, e.g., by fixing vacuum tube 127 to a more stationary object such as a rib spreader. Device 120 and similar devices described herein can be used to stabilize the heart in a similar manner by grasping the apex and/or other suitable locations on the heart, such as the anterior interventricular groove, and attaching the device to a stationary object. In this manner, it is possible to use one or more devices such as device 120 and similar embodiments in concert with the various embodiments of tissue ablation templates described herein placed at a variety of suitable locations on the heart to create a relatively stable epicardial surface for ablation. Such stabilization allows the surgeon to complete the manual ablation or other surgical procedures more easily and more quickly than without stabilization. For example, using a first device 120 on a suitable ventricular surface and a second device 120 on the apex permits the surgeon to elevate the heart and stabilize it to permit ablation with an ablation template on the posterior side of the heart. Addition of a flexible joint between vacuum tube 127 and member 121 may allow the heart to maintain its normal movement resulting from contraction further reducing trauma to the heart.

In some embodiments, device 120 and an ablation template device as described herein may be appropriately miniaturized to permit deployment via port-access methods, such as small thoracotomies. An ablation template device as described herein also could be appropriately miniaturized for application on the endocardial surface of the heart, e.g., using transluminal approaches. For endocardial application, an ablation probe such as an RF antenna can be integrated with the ablation template device, which could be made substantially flexible but incorporate shape memory elements or elasticity to expand following transluminal deployment.

In alternative embodiments, no external vacuum pressure need be applied. Instead, as shown in the cross-sectional side view of FIG. 12, a device 120' can be configured to incorporate a mechanical structure that permits variation of the volume within the chamber 123', e.g., by actuation of a piston-like member or modulation of a fluid chamber. For example, a shaft 130 can be mounted within chamber 123' substantially where vacuum port 125 and vacuum tube 127 are located in FIG. 11. A distal end 131 of the shaft 130 is positioned to engage a flexible membrane 132 within chamber 123'. An attachment pad can be placed between distal end 131 of shaft 130 and flexible membrane 132 to permit adhesive or thermal attachment. Upon actuation of the shaft 130, the membrane.132 can be moved inward and outward relative to the interior of chamber. 123', and thereby change the volume and, as a result, pressure within the chamber 123'.

Figure 12:
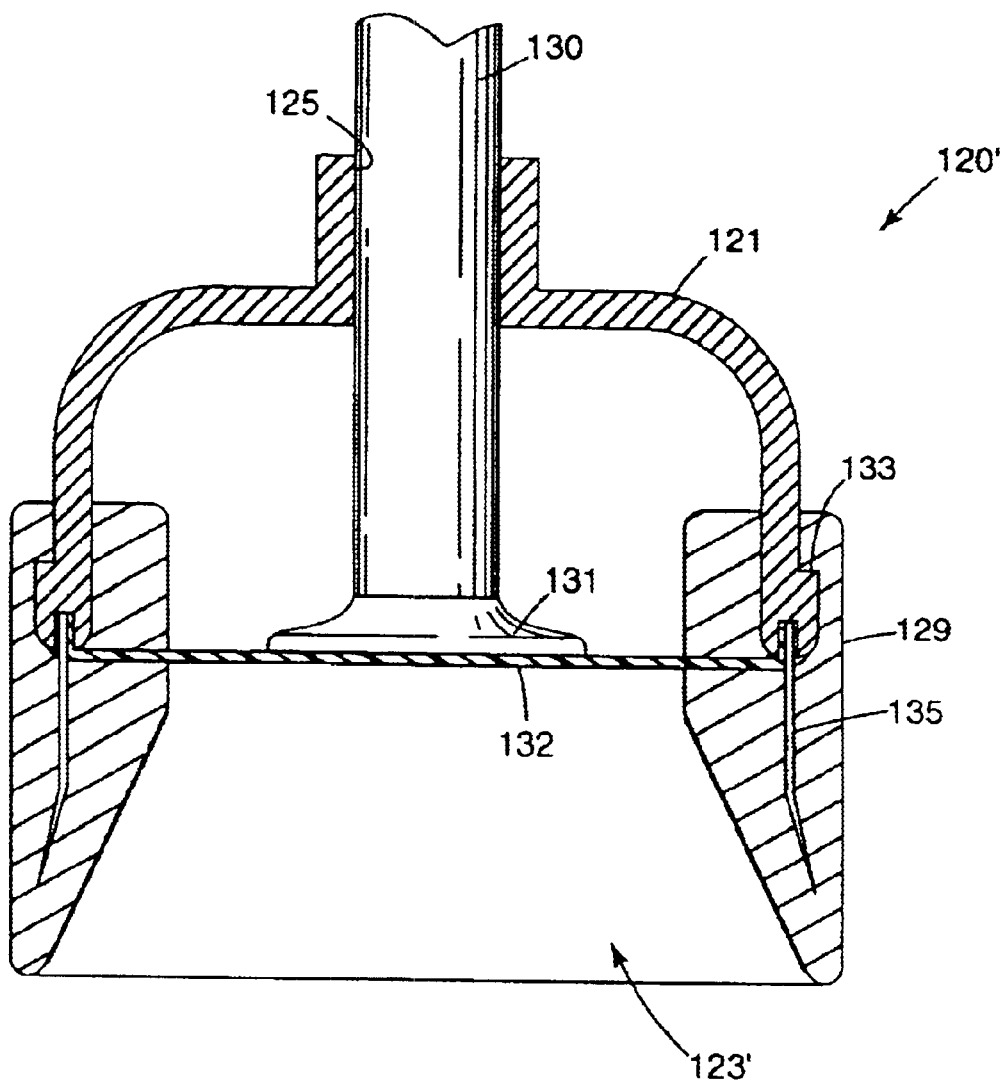
FIG. 12 is a cross-sectional side view of a cup-like manipulation device.

As an illustration, upon engagement of seal member 129 with heart 10, shaft 130 and cup 121 are pushed onto heart surface 15. Retracting shaft 130 draws membrane 132 and heart surface 15 into the chamber defined by cup 121. Upon release of shaft 130, elasticity of membrane 132 biases the membrane and shaft 130 back to their original positions, increasing the volume and decreasing the pressure within chamber 123'. As a result, chamber 123' produces a suction effect without application of external negative pressure that enhances the seal provided by the tacky skirt-like member 129. Thus, the shaft 130 and membrane 132 can be used to create a negative pressure within chamber 123' that serves to aid adhesion of the tacky skirt-like gasket member 129 to apex 122 (shown in FIG. 11). FIG. 12 also illustrates internal attachment of skirt-like member 129 with cup frame 121. In particular, as shown in FIG. 12, skirt-like member 129 can be molded about the outer lip 133 of cup frame 121. Also, an insert 135 formed from a metal or polymeric material can be embedded within cup frame 121 and skirt-like member 129 to provide added structural integrity to device 120'.

Figure 13:
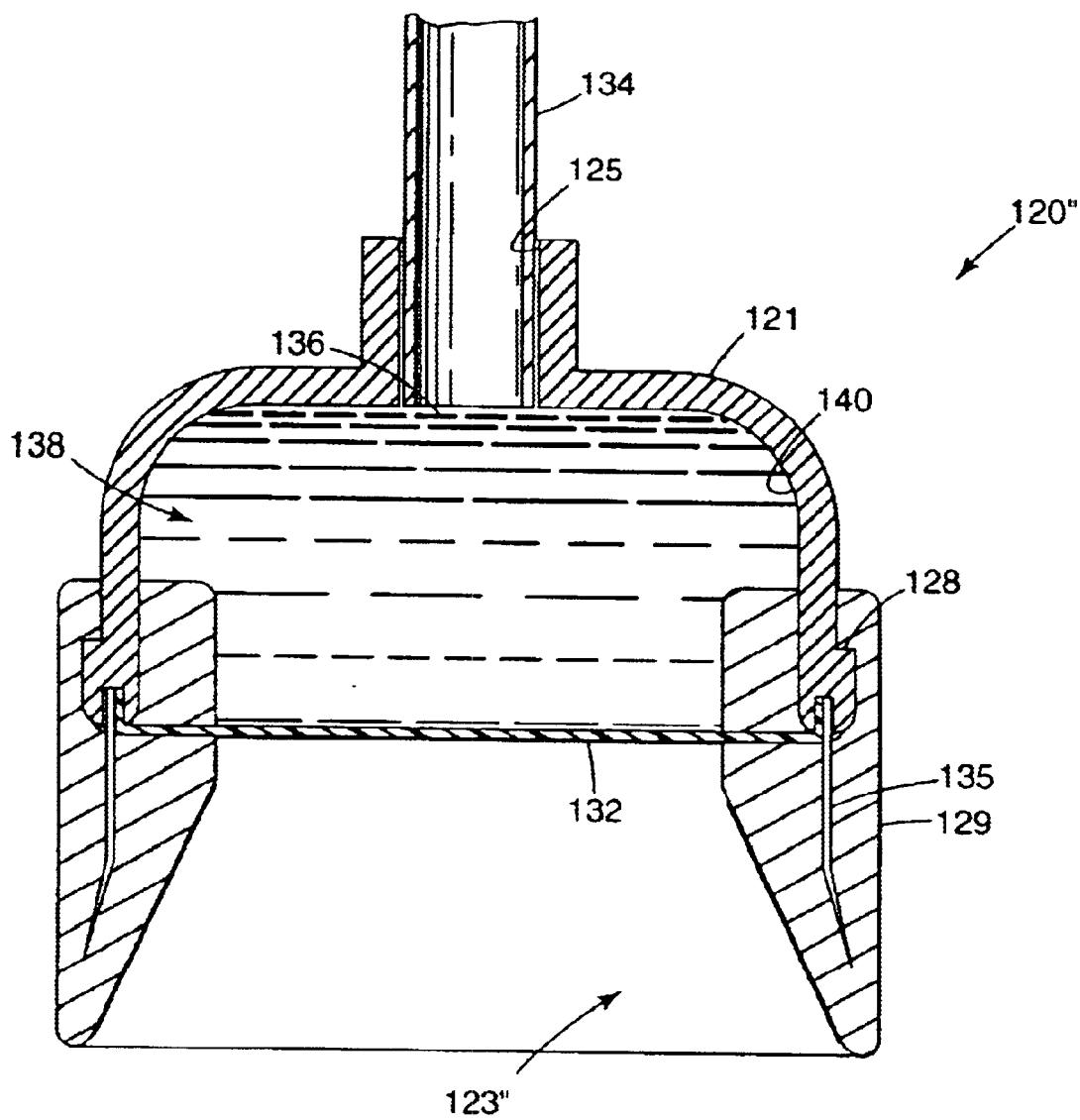
FIG. 13 is a cross-section side view of another cup-like manipulation device.

FIG. 13 illustrates another embodiment of a device 120' incorporating a limpet-like structure. In the example of FIG. 13, instead of a shaft 130 as shown in FIG. 12, chamber 123 receives a fluid tube 134 at port 125. Fluid tube 134 permits inflow and outflow of fluid 136 into the internal cavity 138 defined by membrane 132 and the inner wall 140 of chamber 123. In this case, internal cavity 138 can be normally filled with a fluid 136 such as saline. When fluid is drawn from device 120 through fluid tube 134, membrane 132 is drawn toward port 125, decreasing the volume of the portion 138 of chamber 123 that engages heart 10. In this manner, pressure within chamber 123 is reduced, creating a suction effect that aids the sealing pressure of skirt-like member 129 at apex 122. A stopping mechanism such as a valve or stopcock (not shown) may be employed to stop the flow of fluid through fluid tube 134, and thereby fixing the sealing pressure.

Figure 14:
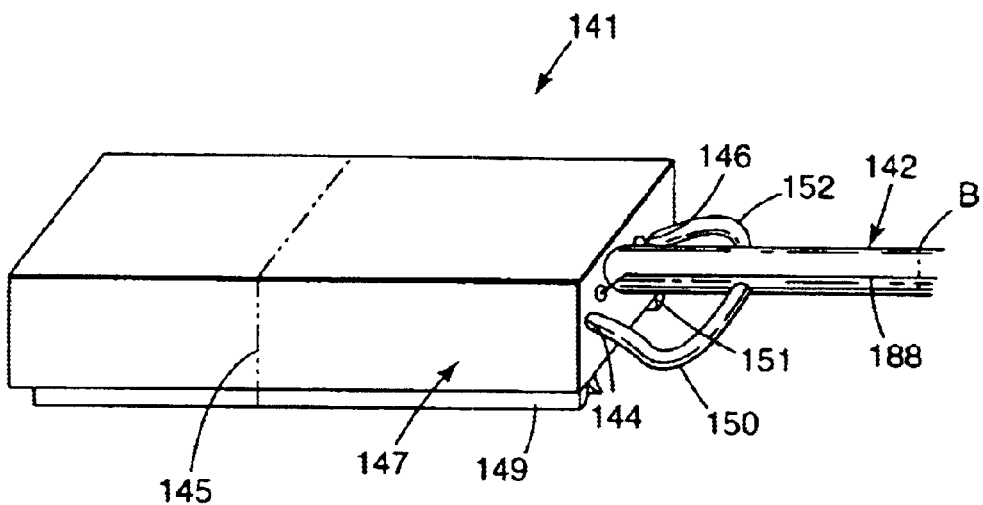
FIG. 14 is a perspective view of an ablation template device incorporating structure for accommodating an ablation probe.
Figure 15:
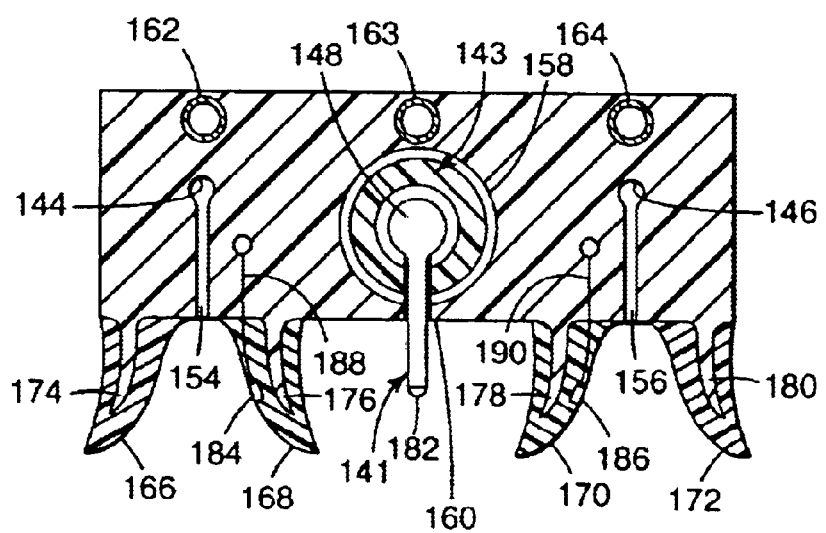
FIG. 15 is a cross-sectional view of the device of FIG. 14, taken at point 145.

FIG. 14 depicts a device 141 that permits attachment of an antenna for delivery of radio frequency (RF) energy to the surface of a heart for the purpose of creating a linear lesion of dead tissue that is transmural. FIG. 15 shows a cross section at point 145 on device 140 of FIG. 14. The body 147 of the device 140 can be made of a suitable flexible polymeric material such as silicone elastomer. A shaft 142, made of either a rigid or flexible material, depending upon application, can be used to position the device 140 in either an-open or minimally invasive surgical procedure. The diameter of shaft 142 would be sized differently for each of these applications. In the example of FIGS. 14 and 15, shaft 142 also contains a moveable inner catheter 143 that contains the RF antenna and, if appropriate, a fluid delivery lumen 148. In addition to the catheter 143, shaft 142 can provide a vacuum connection to device 140, which may define one or more inner chambers. The device 140 can be attached to the heart using two vacuum ports 144, 146 connected to one or more seal members 149, 151. Vacuum pressure can be provided to ports 144, 146 via tubes 150, 152, which are coupled to an external vacuum source and branch off from shaft 142.

The body 147 of device 140 can be molded to define two vacuum chambers 154, 156 and a central lumen 158, which opens to a base side 160 of the device and forms a continuous track for accommodation of catheter 143. Malleable metal shafts 162, 163, 164 can be inserted into the body 147 to provide shaping capability and added structural integrity, but may not be necessary to achieve compatibility with all desired contours and positions on the heart. Vacuum pressure delivered through vacuum chambers 154, 156 via vacuum ports 144, 146 is used to attach the device 140 to the heart. Flexible seal members 166, 168, and 170, 172 are disposed adjacent each vacuum chamber 154, 156, respectively, and conform to the surface of the heart and function as seals 149, 151. Seal members 166, 168, 170, 172 can be made of silicone elastomers as soft as 5 on the Shore A scale, or can be made of silicone gel. A suitable silicone elastomer material may have a durometer, for example, in the range of 5 to 30 Shore A. An example of one suitable silicone gel material is MED 6340, commercially available from NUSIL Silicone Technologies, of Carpinteria, Calif. The MED 6340 silicone gel is tacky and exhibits a penetration characteristic such that a 19.5 gram shaft with a 6.35 mm diameter has been observed to penetrate the gel approximately 5 mm in approximately 5 seconds. This penetration characteristic is not a requirement, but merely representative of that exhibited by the commercially available MED 6340 material. These materials can conform to the irregular shape of the myocardium under negative pressure created by the vacuum source and, if formed from silicone gel, may provide tackiness that aids the seal.

The seal members 166, 168, 170, 172 can be partially shaped and stiffened, if necessary by fins 174, 176, 178, 180, respectively, placed at different intervals along the length of the seal members. These fins can be made of flexible metal or can be part of the material forming body 147 of device 140 and integrally molded therewith. Seal members 166, 168, 170, 172 and associated vacuum chambers 154, 156 may extend along the length of body 147, like central lumen 158, to define elongated tracks. Upon application of vacuum pressure to vacuum ports 144, 146, vacuum chambers 154, 156 serve to hold device 140 tightly against the surface of the heart. Device 140 may be sized and structured to provide a local stabilizing effect on the tissue to which the device is attached, e.g., for beating heart surgical applications. In many embodiments, however, stabilization will not be necessary. Rather, it is sufficient that device 140 fix a surgical instrument, e.g., RF antenna 141, in the same frame of motion as the moving tissue. In this manner, an instrument can be applied with precision to the surface of the heart without significant relative motion.

In the central lumen 158 is inserted catheter 143, which, in the example of FIGS. 14 and 15, contains RF antenna 141. Antenna 141 may, itself, enclose fluid delivery lumen 148. RF antenna 141 is shown in FIGS. 14 and 15 at the end of catheter 143, where the antenna emerges at an angle to the catheter and protrudes through the track defined by central lumen 158 of device 140. By sliding catheter 143 along the track defined by lumen 158, the tip 182 of antenna 141 can move along the track and deliver energy to the tissue with which it is in contact, creating a lesion that can extend the full thickness of the myocardium. An RF antenna is one example of an ablation probe suitable for use with device 140 to ablate tissue. Other ablation instruments could be placed in catheter 143, however, including laser, ultrasonic, and cryogenic probes, all, all of which could create a lesion in a similar fashion.

In some embodiments, catheter 143 can be moved through lumen 158 either manually by a surgeon by grasping the proximal end of the catheter or by a mechanical device connected to the catheter, e.g., at its distal end. For example, a variety of electrical motors could be used to drive catheter 143 along central lumen 158, e.g., directly via a worm gear drive or indirectly via pulley or gear arrangements. The motors can be driven either automatically, or at the direction of the surgeon using a joystick or other manual controls. Electrodes 184, 186 can be mounted on an inner surface of the innermost seal members 168, 170 for contact with the myocardium. Electrodes 184, 186 are connected to conductors 188, 190, respectively, which extend out of device body 147 and continue into shaft 142. Electrode 184 and conductor 188 on one side of the device 140 can be used to send an electric signal across the lesion area formed by antenna 141 for detection on the other side of the device by another electrode 186 and conductor 190.

Figure 16:
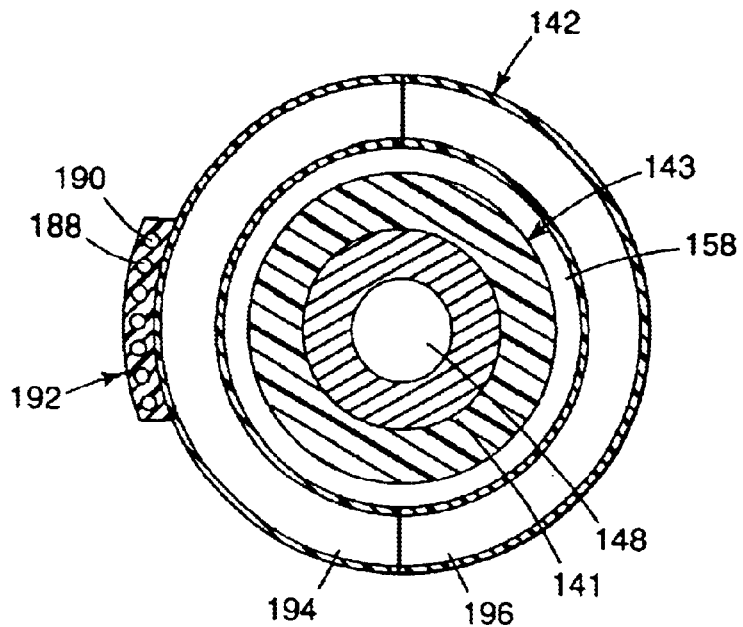
FIG. 16 is a cross-sectional view of a shaft incorporated in the device of FIG. 14, taken at point B.

FIG. 16 is a cross section at point B on shaft 142 of FIG. 14. Conductors 188, 190 can be connected via a cable 192 to appropriate instrumentation. Such conductor/electrode sets can be used to measure impedance across the lesion or conduction velocity across the lesion. These measurements can be used to determine if the lesion is truly transmural, that it extends the full thickness of the myocardium. Conductors 188, 190 can be ultimately connected to an external control unit which is capable of using impedance or conductance time or velocity measurements to generate either a signal observable by the surgeon or a signal for control of a device responsible for advancing catheter 143 along central lumen 158 when a transmural lesion has been created in one region. To that end, a plurality of electrodes 184, 186 can be placed on respective sides of central lumen 158 to take measurements at several positions along the length of the lesion track, thereby driving controlled advancement of catheter 143 as an effective lesion is formed at each position. Again, advancement of catheter 143 can be automated or manual. In either case the surgeon can be assured during the procedure that an effective lesion has been formed.

As shown in FIG. 16, outer shaft 142 may contain two separate lumens 194, 196, which provide vacuum pressure to chambers 154, 156 via tubes 150, 152. FIG. 16 also shows a cable with a wiring bundle including conductors 188, 190, for electrical communication with electrodes 184, 186 (FIG. 15). The number of conductors may be dependent upon the number of electrodes placed on each side of the inner sealing members 168, 170. For example, each electrode 184, 186 preferably is coupled to an individual conductor 188, 190, respectively. Alternatively, a single continuous electrode could be disposed on one side of central lumen 158 and coupled to a single conductor. In this case, a series of electrodes at various positions on one side of central lumen 158 would transmit signals to the continuous electrode on the other side or vice versa. Catheter 143 fits in the central lumen 158 of shaft 142 and, in this example, contains RF antenna 141 and fluid lumen 148. Again, other embodiments could have different types of ablation probes built into catheter 143.

Figure 17:
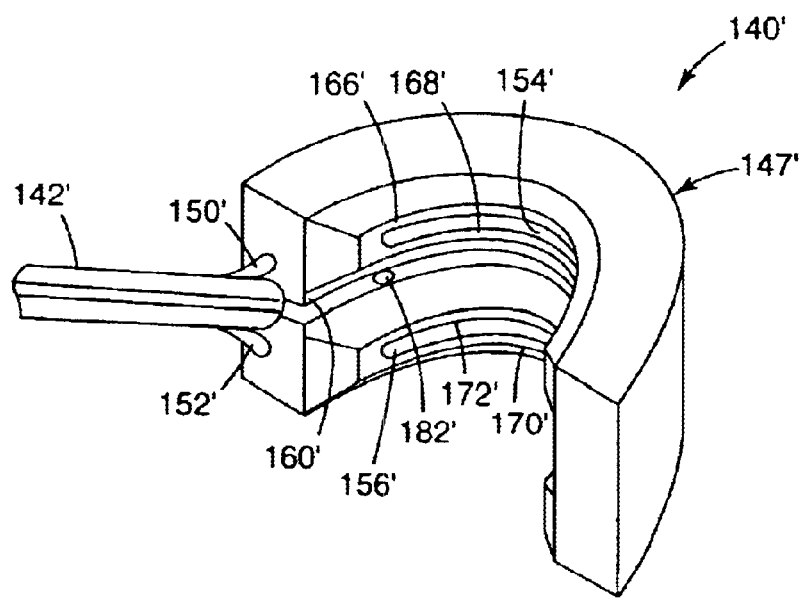
FIG. 17 is a perspective view of an arcuate ablation template device incorporating structure for accommodating an ablation probe.

FIG. 17 shows a specialized form of a device 140' as shown in-FIG. 14. In this embodiment, the device body 147' is shaped in a substantially semicircular form to facilitate contact around the base of the pulmonary vein or similar structure. Device body 147' is moved into position via shaft 142' and vacuum is used to affix it to its first location on the vein. In this case, a catheter is translated around the arcuate path defined by a central lumen. The catheter carries an RF antenna or other ablation probe that is exposed via opening for contact with the outer wall of the pulmonary vein. Lesion generation is carried out on the full thickness of the vein wall in one location by energization of the RF antenna or activation of other suitable probe. As shown in FIG. 17, vacuum pressure can be applied via vacuum chambers 154', 156' with seal members 166', 168', 170', 172' providing an effective seal. When vacuum pressure is released, device 140' can be moved via shaft 142' to another location to create a lesion continuous with the previous one until a circumferential lesion is created all the way around the base of the pulmonary vein. As in the example of FIGS. 14–16, device 140 can be fixed in the same frame of motion as the pulmonary vein, eliminating significant relative motion to enhance precision in creation of the lesion. The interior of device 140' is identical to that of device 140 as shown in FIG. 15, with two modifications. The malleable metal inserts 162, 164 are replaced with shaped memory metal inserts, which cause 140' to assume an arcuate shape shown in FIG. 17. Malleable insert 163 is replaced with a semi-rigid metal rod which can be withdrawn through shaft 142' to allow elements 162, 164 to assume their arcuate shape and cause device 140' to also assume an arcuate shape. Insertion of the semi-rigid rod causes device 140' to straighten into a linear shape that would permit device 140' to entry into or withdraw from a tubular access port used in minimally invasive surgical procedures.

Although device 140 is depicted as having a "shepherd's crook" shape, that shape is merely an exemplary embodiment of the invention. The ablative device may take other forms such as a loop, hook, ess or snare. In any of these configurations, electrode sets may be placed on the device so as to have a one or more transmitting electrodes on one side of the lesion and one or more receiving electrodes on the opposite side of the lesion to measure the effectiveness of the ablation.

Figure 18:
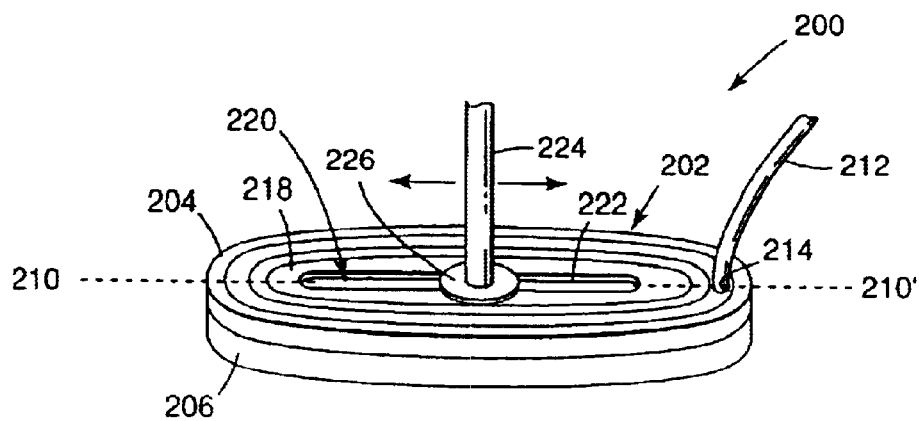
FIG. 18 is a perspective view of an added ablation template device incorporating structure for accommodating an ablation probe.
Figure 19:
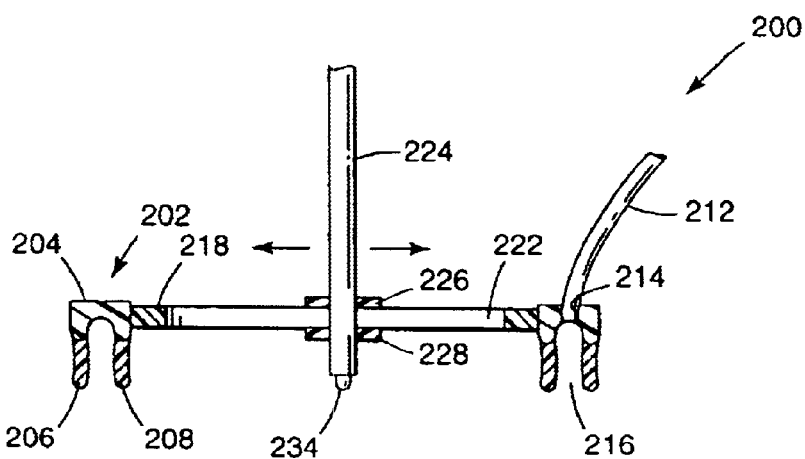
FIG. 19 is a cross-sectional view of the device of FIG. 18, taken along line 210–210'.
Figure 20:
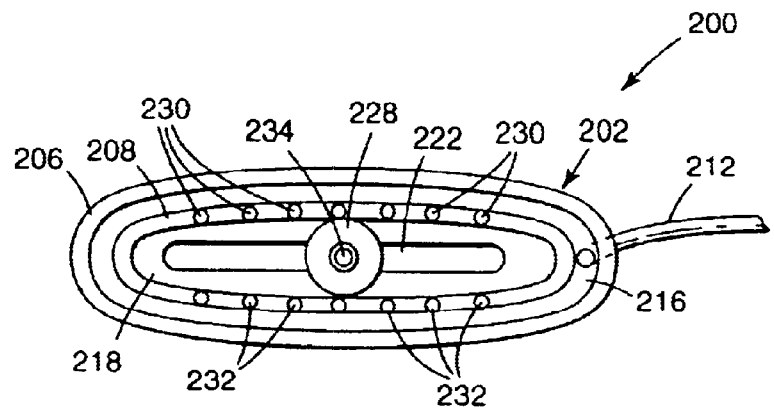
FIG. 20 is a bottom view of the device of FIG. 18.

FIGS. 18–20 illustrate another embodiment of an ablation template device 200. FIG. 18 is a perspective side view of device 200. FIG. 19 is a cross-sectional side view of device 200 taken at line 210–210' in FIG. 18. FIG. 20 is a bottom view of device 200. As shown in FIGS. 18–20, device 200 includes a ring-like contact member 202 defining an annular but generally oval-shaped chamber 204. Contact member 202 may include a frame 204 formed from a semi-rigid material, and seal members 206, 208 formed at the inner and outer diameters of frame 204. Seal members 206, 208 can be formed, for example, from a silicone gel material. A vacuum tube 212 is mounted in a vacuum port 214 that communicates with an interior chamber 216 defined by frame 204 and seal members 206, 208. A cover 218 can be mounted within the central aperture 220 defined by frame 204, or integrally formed with the frame, e.g., by molding. Cover 218 includes a slot-like track 222 that extends along the major axis of contact member 202. Track 222 accommodates an ablation probe 224.

Ablation probe 224 may take the form of an RF, laser, ultrasonic, or cryogenic probe, and includes upper and lower flanges 226, 228 that hold the probe within track. In particular, upper flange 226 bears on an upper surface of cover 218 adjacent track 222, while lower flange 228 bears on a lower surface of the cover. Ablation probe 224 is slidable along track 222, however, to define a lesion path for an ablation procedure. In particular, a surgeon can simply slide ablation probe 224 along track 222. Electrodes 230, 232 on opposite sides of track 222 can be electrically coupled to electronics that provide measurements, e.g., impedance, conduction velocity, and conduction time, to assess the effectiveness of the ablation procedure. In response to indications provided based on the electrode measurements, the surgeon advances ablation probe 224 along track 222. Alternatively, ablation probe 224 can be advanced automatically along track 222 in response to such indications. In some embodiments, tip 234 of ablation probe 224 may contact tissue.

Figure 21:
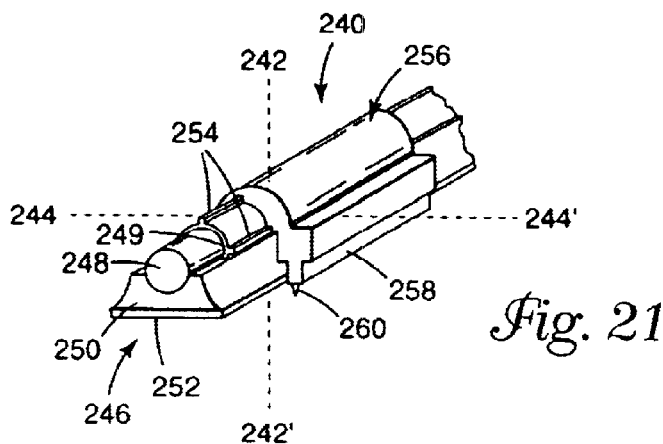
FIG. 21 is a perspective view of an ablation template device incorporating a movable carriage for support of an ablation probe.
Figure 22:
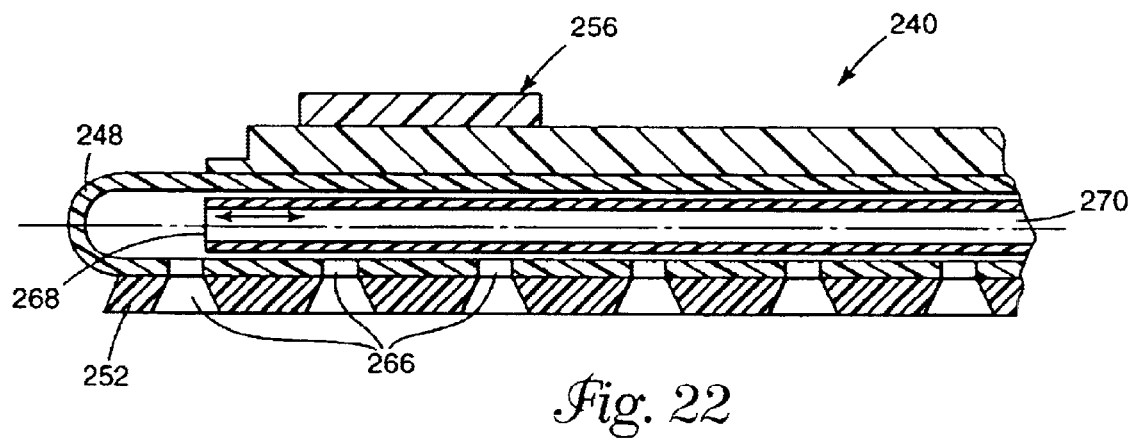
FIG. 22 is a cross-sectional view of the device of FIG. 21, taken along line 250–250'.
Figure 23:
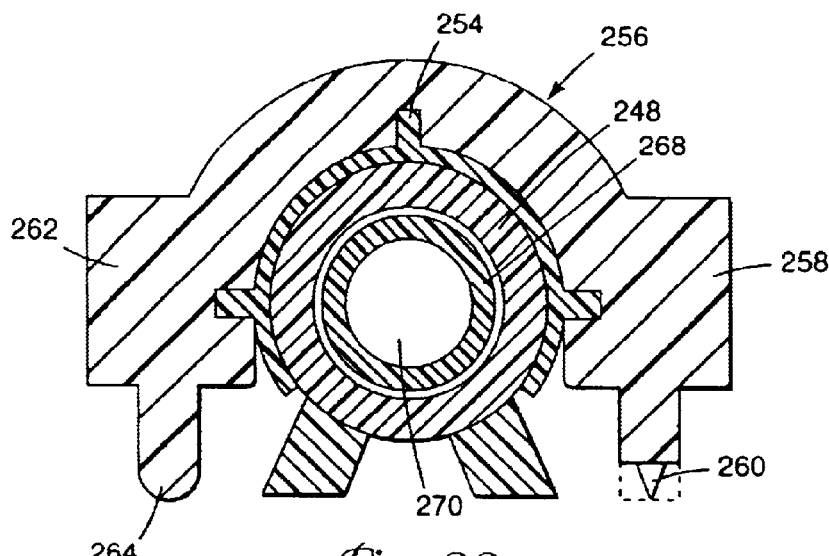
FIG. 23 is a cross-sectional view of the device of FIG. 21, taken along line 244–244'.

FIGS. 21–23 illustrate another ablation template device 240. FIG. 21 is a partial perspective view of device 240. FIG. 22 is a partial cross-sectional side view of device 240 of FIG. 21 taken at line 242–242'. FIG. 23 is a cross-sectional front view of device 240 of FIG. 21 taken at line 244–244'. As shown in FIGS. 21–23, device 240 includes a contact member 246 mounted on an elongated guide member 248 that extends through bore 249. Contact member 246 may be slidable along guide member 248 or fixed. The contact member includes a frame 250 formed of a flexible material, and a seal member 252 formed from a compliant, tacky material such as silicone gel. The seal member 252 interfaces with tissue, e.g., on the surface of the heart. Frame 250 further defines one or more rails 254 that extend radially outward relative to contact member 246 and longitudinally relative to guide member 248. A carriage 256 is mounted on rails 254, e.g., via inner grooves that engage the rails, and defines a lateral flange 258 designed to hold an ablation probe 260. As shown in FIGS. 21 and 23, in particular, ablation probe 260 protrudes downward from lateral flange 258 for contact with organ tissue.

Ablation probe 260 can be molded into or otherwise encased in lateral flange 258 of carriage 256. A second lateral flange 262 (FIG. 23) can be provided, along with a counter probe 264, to contact tissue and thereby balance device 240 on a side of carriage 256 opposite lateral flange 258. Ablation probe 260 may take the form of an RF, laser, ultrasonic, or cryogenic probe designed to ablate tissue. Ablation probe 260 may have electric conductors that run along the length of guide member 248 to an external power supply, in the case of an RF or ultrasonic probe. Alternatively, an optical fiber or fiber bundle may be coupled between ablation probe 260 and an external source of laser energy. As a further alternative, a fluid line may extend between ablation stylus and a cryogenic source. In each case, device 240 can be sized and arranged to permit deployment by endoscopic or other minimally invasive techniques to an ablation site, e.g., on the surface of the heart. Thus, in one application, device 240 can be deployed and affixed to the surface of a beating heart, and fix the ablation probe 260 in the same frame of motion as the heart.

Seal member 252 may define a plurality of vacuum ports 266 coincident with vacuum ports in guide member 248. A vacuum tube resides within an inner lumen 270 of guide member 248 and includes one or more output ports that apply vacuum pressure to vacuum ports 266. To perform an ablation procedure, device 240 is deployed to a desired site on the surface of an organ such as the heart. Vacuum pressure is applied to affix contact member 246 to the tissue surface via the seal interface provided by seal member 252. At the same time, ablation probe 260 is brought in contact with the tissue surface. Ablation probe 260 is then energized to ablate the local tissue area proximate the tip of the probe. A guide wire or other elongated member can be coupled to carriage 256, which preferably is slidable along rails 254 defined by contact member 252. By translating the guide wire, carriage 256 can be moved relative to contact member 252 and thus relative to the tissue surface, thereby creating an ablation track. As in other embodiments, electrodes can be integrated with seal member 252 to measure the extent of ablation. Again, the measurements can be used as the basis for manual or automated control of the guide wire, and resulting movement of carriage 256.

Figure 24:
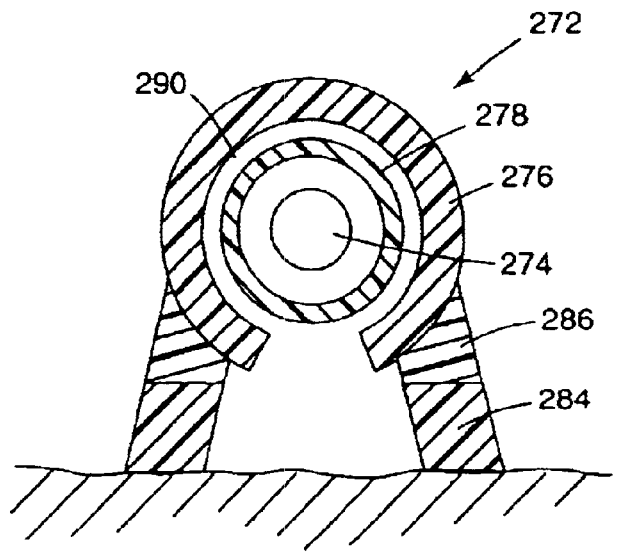
FIG. 24 is a cross-sectional front view of an ablation template device having an internal ablation probe.
Figure 25:
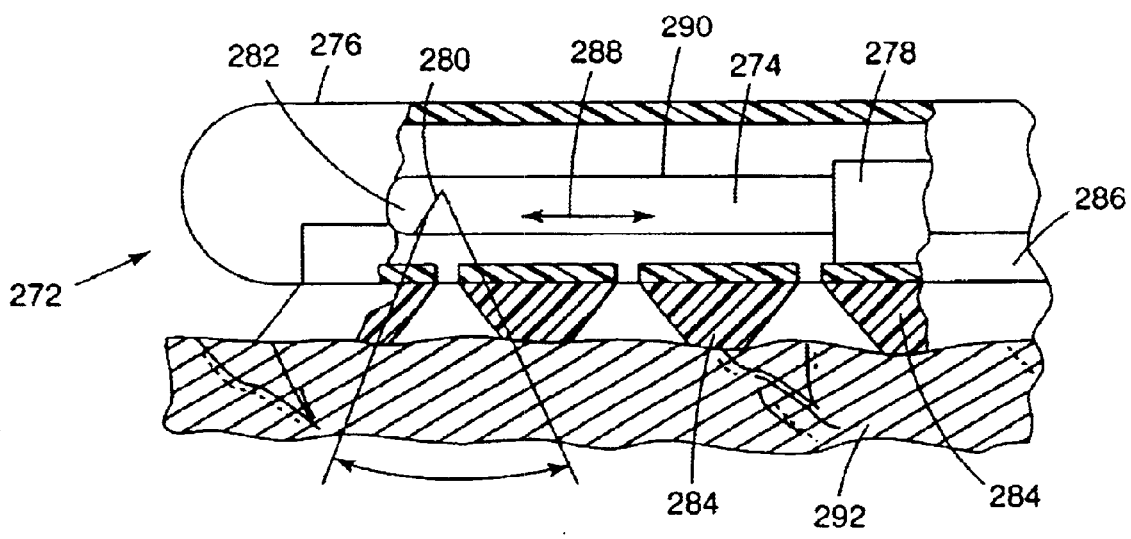
FIG. 25 is a cross-sectional side view of the ablation template device of FIG. 24.

FIGS. 24 and 25 illustrate another ablation template device 272. FIG. 24 is a cross-sectional front view of device 272, while FIG. 25 is a fragmentary cross-sectional side view. Device 272 is somewhat similar to device 240 of FIGS. 21–23. However, device 272 need not incorporate a carriage. Rather, device 272 provides an internal optical waveguide 274 mounted within a guide member 276 that transmits laser radiation. Waveguide 274 may be housed in a cannula 278. Waveguide 274 may incorporate a reflector 280 at its distal end 282 that reflects laser energy downward through a chamber defined by seal member 284 to ablate tissue. Seal member 284 may be substantially compliant and tacky and may be attached to a semi-rigid frame 286 that is coupled to or integrated with guide member 276. Cannula 278 and waveguide 274 preferably are movable along the length of guide member 276, as indicated by arrow 288. Optical waveguide 274 can be mounted within an outer vacuum lumen 290 that delivers vacuum pressure to affix device 272 to the tissue 292 via seal member 284. To form an ablation track, optical waveguide 274 can be translated within guide member 276, as indicated by arrow 288. Once again, electrodes can be integrated with seal member to enable manual or automated control of waveguide movement.

Ablation, and measurement of impedance or conduction time to assess ablation lesion depth, can also-be performed along the interior surfaces of a structure. For example, a linear RF electrode can be transluminally introduced via a catheter into the atria of the heart and positioned on the endocardium in appropriate locations. Ablative energy from the RF electrode can then be applied. Electrode sets used to measure impedance or conduction time or other electrical properties can be integrated into the catheter body parallel to but insulated from the active RF electrode at the distal end of the catheter. These electrode sets can be utilized as described above to both measure lesion depth (from the endocardial to the epicardial surface) and to control delivery of energy.

Transluminal introduction, therefore, represents an additional way to create a lesion around the base of the pulmonary veins, and thereby treat atrial fibrillation. The lesion may be created on the interior surfaces of the heart or pulmonary veins, rather than the heart's or veins exterior surfaces. The treatment entails ablating the endocardial tissue near the ostia of the pulmonary veins in the left atrium. Typically the ablation apparatus is delivered to the site on the distal end of a steerable catheter introduced into the atrium or the pulmonary veins, and is manipulated and controlled at the proximal end of the catheter.

Figure 26:
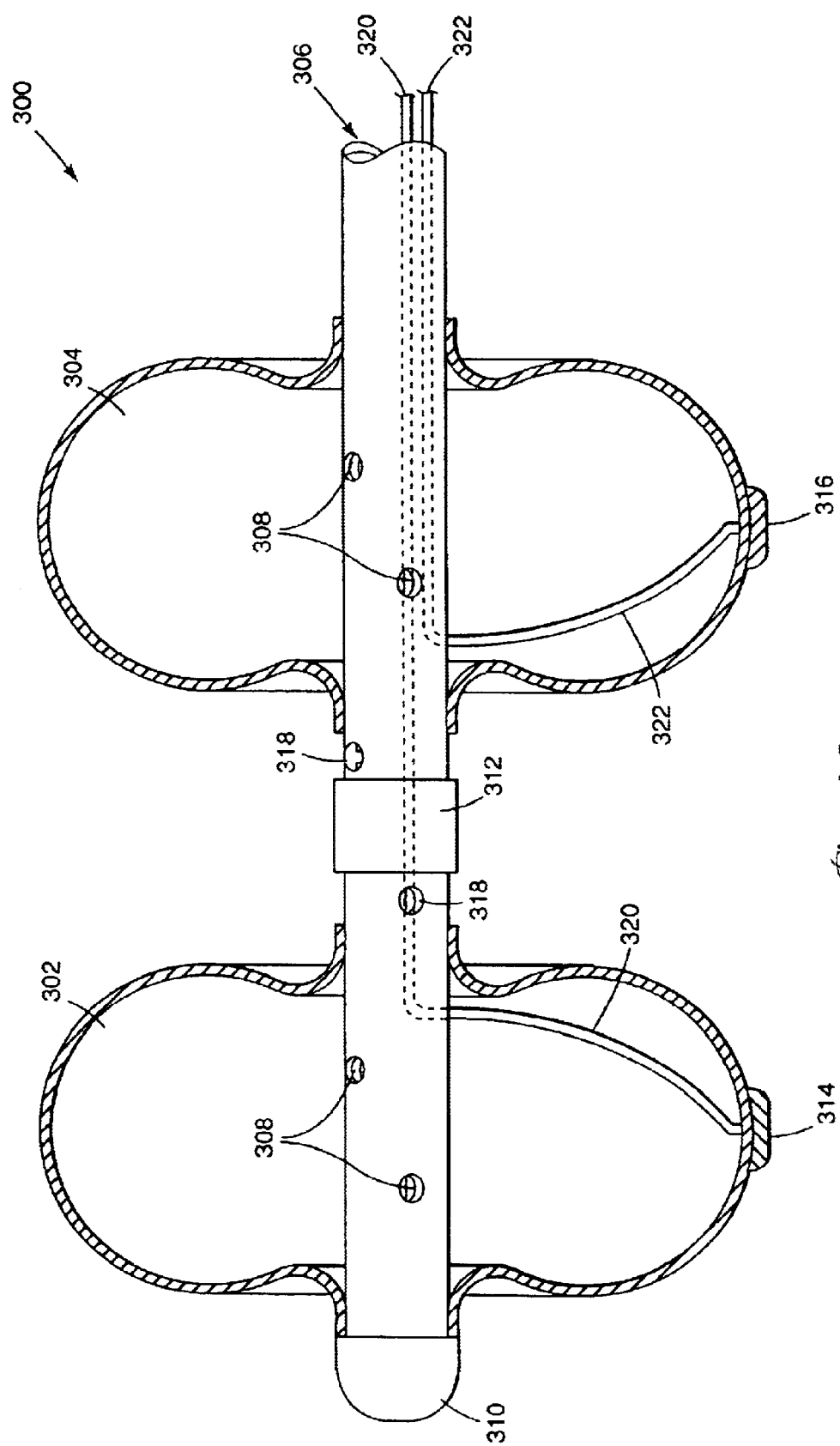
FIG. 26 is a cross-sectional side view of a catheter-mounted ablation device.

FIG. 26 is a side view of an apparatus that may be directed transluminally near the ostia of the pulmonary veins in the left atrium. The device of FIG. 26 may conform substantially to the device shown in U.S. Pat. No. 5,938,660 to Swartz et al. In the example of FIG. 26, however, the device has been adapted in accordance with the present invention to incorporate components for measurement of ablation depth or effectiveness. In particular, electrodes have been positioned on the device so as to come into contact with tissue on opposing sides of a lesion created by the ablative components.

FIG. 26 depicts a distal end of a catheter body 300, with balloons 302, 304 on the catheter body 300 shown inflated. Fluid medium introduced through catheter lumen 306 at the proximal end emerges at the distal end through openings 308, thus inflating the balloons 302, 304. Inflation causes balloons 302, 304 to lodge against the tissue. Catheter 300 may include a tip electrode 310 for sensing electrical activity. Catheter 300 may also include RF electrode 312, which performs the actual ablation. After balloons 302, 304 are inflated, ablation may be accomplished by introducing a conductive media through catheter 300, which emerges at the distal end through openings 318. Application of RF energy follows, and the tissue between the balloons 302, 304 is ablated.

Electrodes 314, 316 are mounted on the surface of the balloons 302, 304 at the circumference of the balloons. Electrodes 314, 316 are insulatively separated from RF electrode 312 and tip electrode 310. Electrodes 314, 316 may be uni-polar or multi-polar. Connecting leads 320 and 322 are coupled to electrodes 314 and 316 respectively. Leads 320, 322 may be wires or conductors printed on the surface of balloons, or a combination of both. Leads 320, 322 travel from electrodes 314, 316 toward proximal end of catheter 300, and emerge from proximal end of catheter where leads are electrically coupled to a measuring device such as an impedance meter or conduction time measuring device. Following measurements that show a successful ablation, the conductive media may be withdrawn, balloons 302, 304 may be deflated, and the catheter may be extracted.

Many variations are possible. For example, a plurality of electrodes can be mounted on the surface of balloons 302, 304. Flexible disks or other extendable members could be used in place of balloons. The RF electrode may be extended or unfolded from the body of the catheter or otherwise steered into proximity with the tissue surface. Ultrasound energy or other energy forms may be used in place of RF. Sites other than the ostium may be treated. In each of these variations, however, electrodes can be used to measure the efficacy of the treatment.

Figure 27:
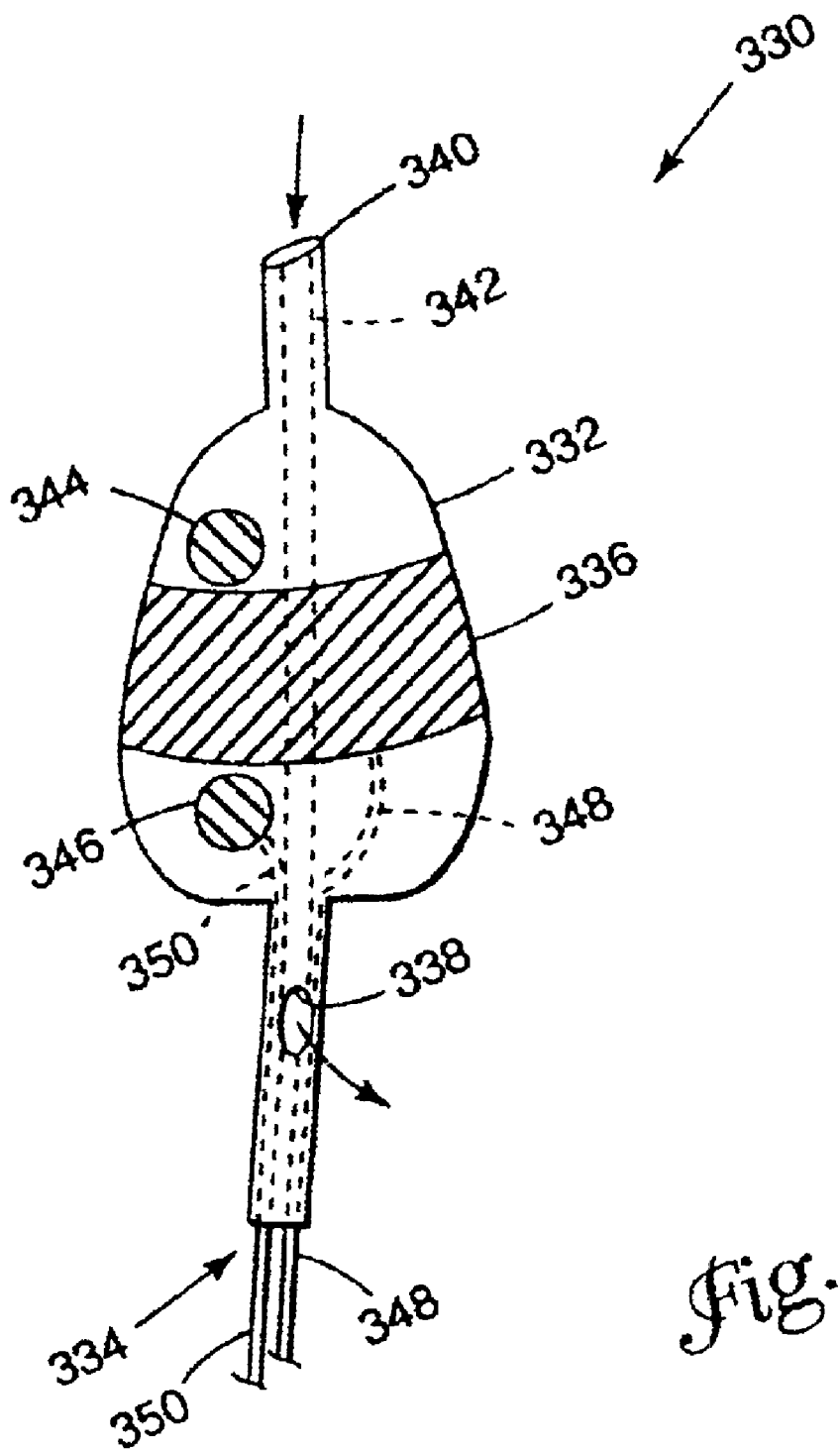
FIG. 27 is a side view of a catheter-mounted ablation device.

FIG. 27 is a side view of an additional apparatus that may be directed transluminally near the ostia of the pulmonary veins in the left atrium. The device of FIG. 27 may conform substantially to the device shown in U.S. Pat. No. 6,024,740 to Lesh et al. and to the device shown in U.S. Pat. No. 6,012,457 to Lesh. In the example of FIG. 27, however, the device has been adapted in accordance with the present invention to incorporate components for measurement of ablation depth or effectiveness. In particular, electrodes have been positioned on the device so as to come into contact with tissue on opposing sides of a lesion created by the ablation element.

FIG. 27 depicts a distal end of a catheter 330, with balloon 332 on the catheter body 330 shown inflated. Fluid medium introduced through catheter lumen 334 at the proximal end inflates balloon 332, causing balloon 332 to lodge against the tissue, preferably but not necessarily at the ostia of the pulmonary veins. Catheter 330 may also include RF electrode 336, which contacts the tissue. Catheter 330 may further include a proximal perfusion port 338 and a distal perfusion port 340 connected by a perfusion lumen 342.

Electrodes 344, 346 are mounted on the surface of balloon 332, and contact the tissue. Electrodes 344, 346 are insulatively separated from RF electrode 336. Electrodes 344, 346 may be uni-polar or multi-polar. A plurality of such electrode pairs could be employed. Connecting leads 348 and 350 are coupled to electrodes 344 and 346, respectively, and travel from electrodes 344, 346 toward proximal end of catheter 330. At the proximal end of catheter, leads 348, 350 are electrically coupled to a measuring device such as an impedance meter or conduction time measuring device. Following measurements that show a successful ablation, the balloon 332 may be deflated and the catheter may be extracted. As with-the apparatus shown in FIG. 26, many variations are possible.

Figure 28:
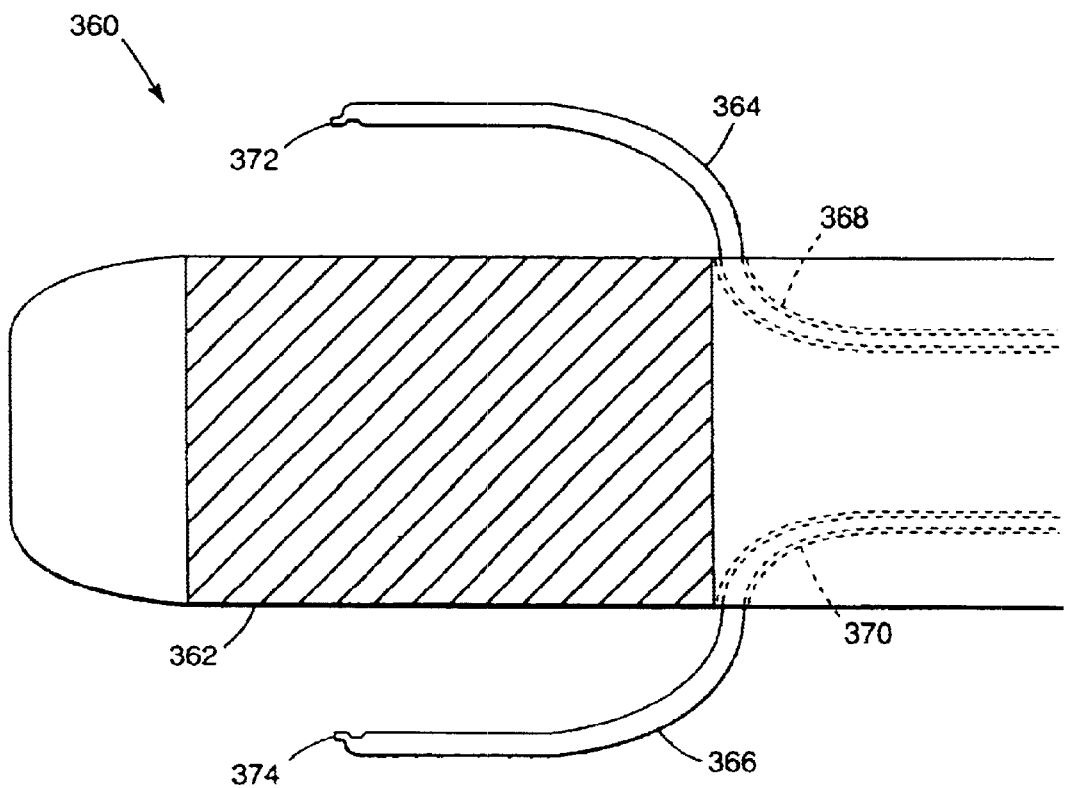
FIG. 28 is a side view of a catheter-mounted ablation device.

FIG. 28 is a side view of a further apparatus that may be directed transluminally to various locations within either atrium. FIG. 28 depicts a distal end of a catheter body 360. Catheter .360 is steerable, allowing it to be positioned against the tissue. An energy delivery means such as an RF electrode 362 performs the ablation.

Electrodes 364, 366 may be independently controlled from the proximal end of the catheter and may be extended from or retracted into lumens 368, 370. Electrodes 364, 366 may be uni-polar or multi-polar. Electrodes 364, 366 extend toward proximal end of catheter 360, where they are electrically coupled to a measuring device such as an impedance meter or conduction time measuring device. Electrode tips 372, 374 can be of various shapes to facilitate insertion into the tissue. For example, electrode tips 372, 374 may have needle-like shapes or screw-like shapes. Being independently extendable and retractable, electrodes 364, 366 may be directed to different sites along a lesion and may be used to make measurements at multiple locations along a lesion. There could also be a plurality of such electrodes to provide electrical measurements at various sites along a lesion.

Figure 29:
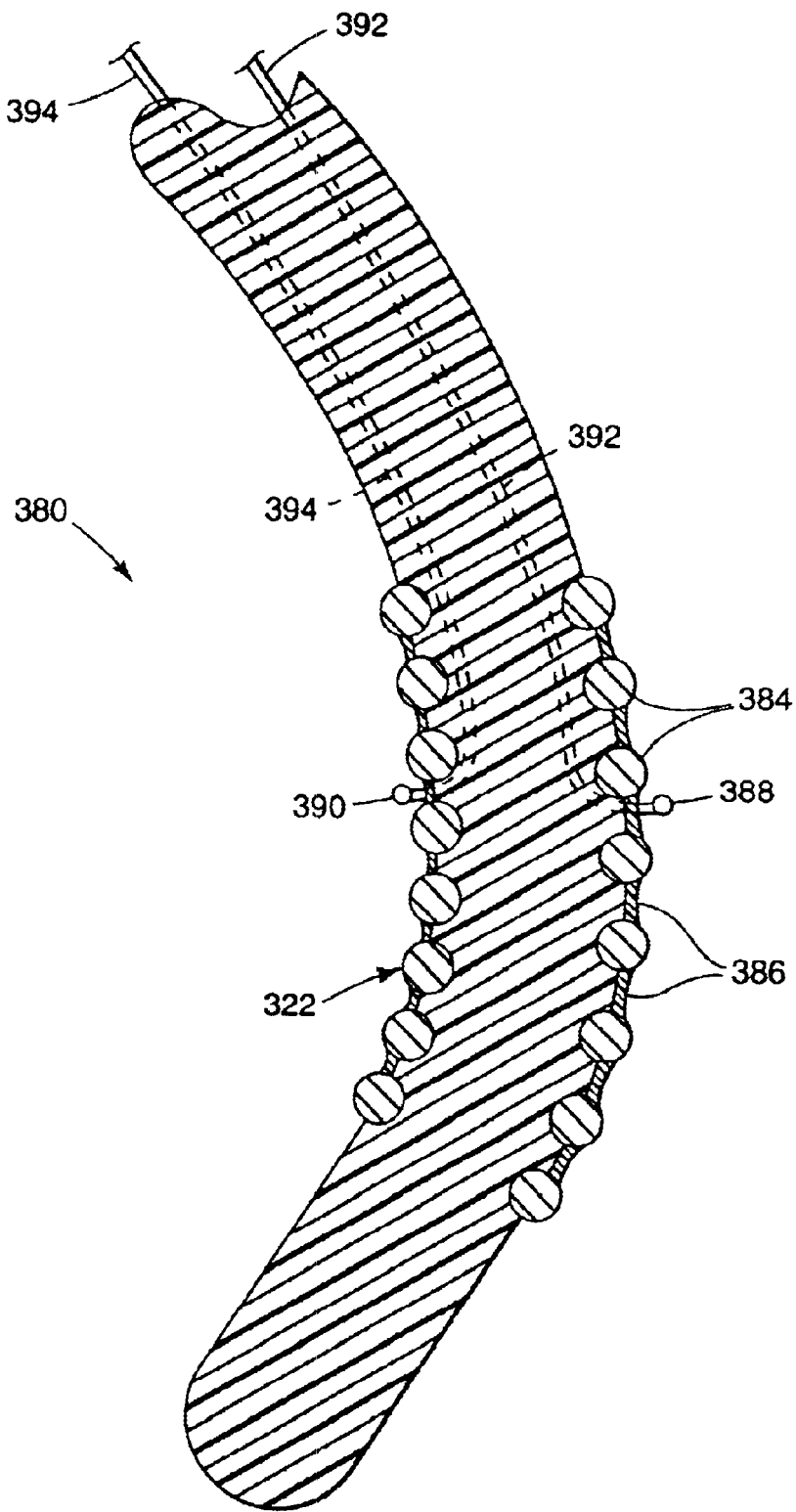
FIG. 29 is a cross-sectional side view of a catheter-mounted ablation device.

FIG. 29 shows another apparatus that may be used transluminally in either atrium. The device of FIG. 29 may conform substantially to the device shown in U.S. Pat. No. 5,676,662 to Fleischhacker et al. In the example of FIG. 29, however, the device has been adapted in accordance with the present invention to incorporate components for measurement of ablation depth or effectiveness. In particular, electrodes have been positioned on the device so as to come into contact with tissue on opposing sides of a lesion created by the helical ablation element.

FIG. 29 shows a distal end of a catheter body 380. Catheter 380 is steerable, allowing it to be positioned against the tissue. An RF electrode 382 in the form of helical coils 384 performs the ablation. Coils 384 are electrically isolated from each other by an insulating substance 386.

Electrodes 388, 390, which may be uni-polar or multi-polar, are mounted on opposing sides of catheter 380 and are electrically isolated from helical coils 384. Electrodes 388, 390 are connected to leads 392, 394, which extend toward proximal end of catheter 380. At the proximal end of catheter, leads 392, 394 are electrically coupled to a measuring device such as an impedance meter or conduction time measuring device.

Figure 30:
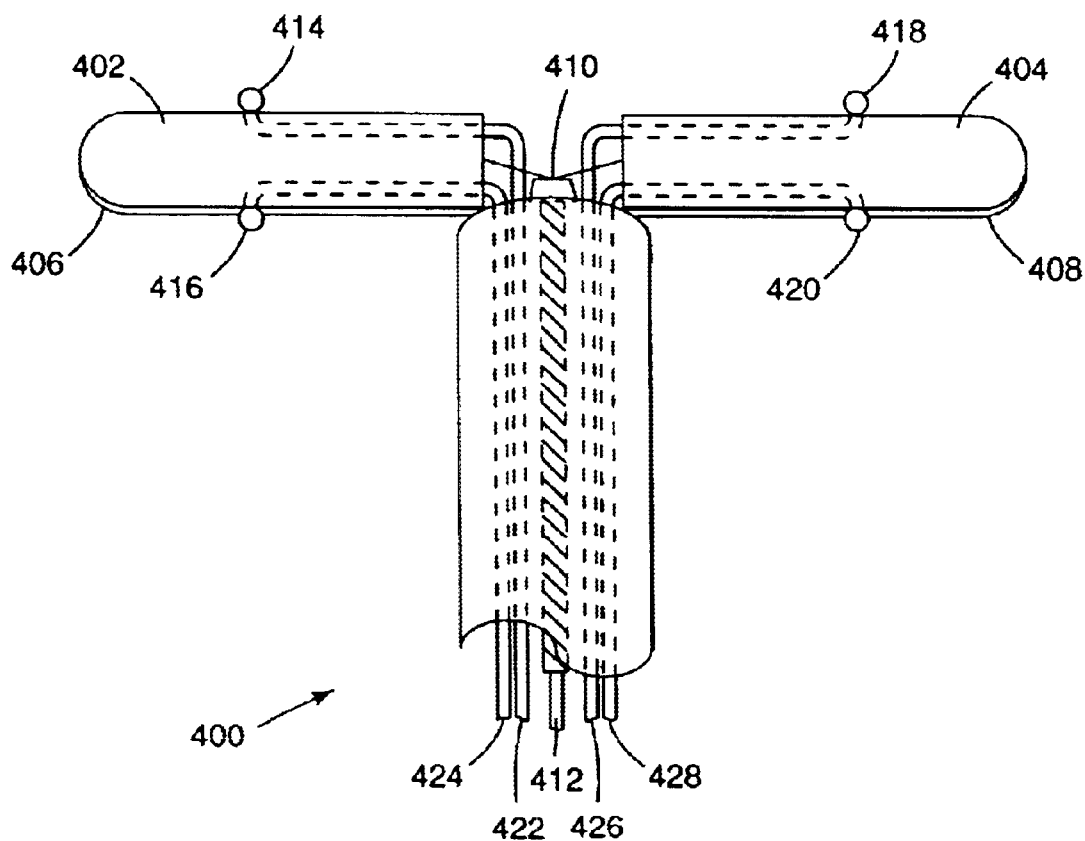
FIG. 30 is a side view of a catheter-mounted ablation device.

FIG. 30 is a side view of a further apparatus that may be directed transluminally, and may also be positioned on the atrial endocardium via thoracoscope or port access. The device of FIG. 30 may conform substantially to the device shown in U.S. Pat. No. 5,916,213 to Haissaguerre et al. In the example of FIG. 30, however, the device has been adapted in accordance with the present invention to incorporate components for measurement of ablation depth or effectiveness. In particular, electrodes have been positioned on the device so as to come into contact with tissue on opposing sides of a lesion created by the ablation elements.

FIG. 30 depicts a distal end of a steerable catheter body 400. Catheter 400 includes two energy delivery surfaces 402, 404 such as RF electrodes, which perform the ablation. Energy delivery surfaces 402, 404 are mounted on movable arms 406, 408 respectively. Arms 406, 408 can be manipulated through a yoke 410, which is coupled to a cable 412 leading to the proximal end of the catheter. By manipulation of cable 412 and yoke 410, arms 406, 408 can be drawn into the tip of catheter body 400 and placed in a closed position parallel to catheter body 400. Cable 412 may also be used to supply power to energy delivery surfaces 402, 404. Arms 406, 408 can be extended from the tip of catheter body 400 and placed in an open position perpendicular to catheter body 400. When arms 406, 408 are in the open position, catheter 400 can be steered to press energy delivery surfaces 402, 404 against the epicardium or endocardium. Once energy delivery surfaces 402, 404 are in place, energy may be applied to energy delivery surfaces 402, 404 to effect the ablation and create a lesion.

Electrodes 414 and 416 are mounted on opposite sides of arm 406 and electrodes 418 and 420 are mounted on opposite sides of arm 408. Electrodes 414, 416, 418, 420 may be uni-polar or multi-polar. Connecting leads 422, 424, 426 and 428 are coupled to electrodes 414, 416, 418 and 420 respectively, and travel from electrodes 414, 416, 418 and 420 toward proximal end of the catheter. At the proximal end of the catheter, leads 422, 424, 426 and 428 are electrically coupled to one or more measuring devices such as an impedance meter or conduction time measuring device. Leads 422 and 424 carry information pertaining to the lesion created by energy surface 402, and leads 426 and 428 carry information pertaining to the lesion created by energy surface 404.

Many of the devices described above, such as those depicted in FIGS. 28, 29 and 30, may be used with epicardial applications as well as endocardial applications. The devices described above may also be applied to tissues other than cardiac tissues. The electrode sets may be used with or without a surgical template. Although only one set of electrodes is shown in the figures for clarity, a plurality of electrode sets can be used in any embodiment. The electrode sets may be also be deployed independently of the ablative energy delivery system, and may be used with any ablative energy delivery system. Furthermore, in the devices described above, the electrode sets may be used as probes to control the delivery of energy as outlined in FIGS. 4 and 5. The specific embodiments described above are intended to be illustrative of the general principle and are not intended to be limited to a particular device or to a particular template or to a particular ablative energy delivery system.

A number of embodiments of the present invention have been described. Other embodiments are within the scope of the following claims.

What is claimed is:

1. A method for determining the effectiveness of a tissue ablation procedure in ablation conduction paths in the heart, the method comprising:
    prior to ablation, disposing a first electrode on a first side of tissue to be ablated and disposing a second electrode on a second side of the tissue, the second side being opposite the first side following ablation;
    measuring at least one of electrical impedance and electrical phase angle across the ablated tissue; and
    determining the effectiveness of the tissue ablation procedure based on the measurement.

2. The method of claim 1, further comprising measuring the distance between the electrodes.

3. The method of claim 1, further comprising prior to ablation measuring electrical impedance between the electrodes, this measurement to serve as a baseline measurement.

4. The method of claim 1, further comprising prior to ablation measuring phase angle between the electrodes, this measurement to serve as a baseline measurement.

5. The method of claim 1, further comprising calculating an impedance value that will be measured when the tissue ablation procedure has been effectively performed.

6. The method of claim 1, further comprising performing tissue ablation and discontinuing tissue ablation when a predetermined impedance is measured.

7. The method of claim 1, further comprising calculating a phase angle value that will be measured when the tissue ablation procedure has been effectively performed.

8. The method of claim 1, further comprising performing tissue ablation and discontinuing tissue ablation when a predetermined phase angle is measured.

9. The method of claim 1, further comprising:
    making a plurality of measurements of electrical impedance across the tissue during the tissue ablation procedure;

monitoring a decrease in electrical impedance with the measurements; and discontinuing the tissue ablation procedure when the decrease in electrical impedance discontinues.

10. The method of claim 1, further comprising:

making a plurality of measurements of a magnitude of an alternating current phase angle across the tissue during the tissue ablation procedure;

monitoring a change in the magnitude of the phase angle with the measurements; and discontinuing the tissue ablation procedure when the change in the magnitude of the phase angle discontinues.

11. The method of claim 10, wherein monitoring a change in the magnitude of the phase angle with the measurements comprises monitoring a decrease in the magnitude of the phase angle.

12. A method for determining the effectiveness of a tissue ablation procedure in ablation conduction paths in the heart, the method comprising:

prior to ablation, disposing a first electrode on a first side of tissue to be ablated and disposing a second electrode on a second side of the tissue, the second side being opposite the first side following ablation;

measuring at least one of electrical conduction velocity, electrical conduction time, and electrical conduction distance across the ablated tissue as a parameter; and determining the effectiveness of the tissue ablation procedure based on the measured parameter.

13. The method of claim 12, further comprising measuring the distance between the electrodes.

14. The method of claim 12, further comprising prior to ablation, measuring at least one of electrical conduction velocity, electrical conduction time, and electrical conduction distance, this measurement to serve as a baseline measurement.

15. The method of claim 12, further comprising calculating a value that will be measured when the tissue ablation procedure has been effectively performed, of at least one of electrical conduction velocity, electrical conduction time, and electrical conduction distance.

16. The method of claim 12, further comprising performing tissue ablation and discontinuing tissue ablation when a predetermined value is measured of at least one of electrical conduction velocity, electrical conduction time, and electrical conduction distance.

17. The method of claim 12, further comprising:

making a plurality of measurements of the conduction time during the tissue ablation procedure;

monitoring an increase in the conduction time with the measurements; and discontinuing the tissue ablation procedure when the increase in the conduction time discontinues.

18. A method for determining the effectiveness of a tissue ablation procedure, the method comprising:

prior to ablation, disposing a first electrode on a first side of tissue to be ablated and disposing a second electrode on a second side of the tissue, the second side being opposite the first side following ablation;

during the ablation procedure, making a plurality of measurements of conduction time with the first electrode and the second electrode; and determining the effectiveness of a tissue ablation procedure as a function of the measurements of conduction time.

19. The method of claim 18, wherein measuring conduction time with the first electrode and the second electrode comprises:

transmitting a first signal from the first electrode at a first time;

receiving the first signal at the second electrode at a second time; and taking the difference between the second time and the fist time as the conduction time.

20. The method of claim 18, wherein determining the effectiveness of a tissue ablation procedure as a function of the measurements of conduction time comprises:

monitoring an increase in conduction time with the measurements; and determining the full thickness of the tissue has been ablated when the increase in conduction time discontinues.

21. The method of claim 20, further comprising discontinuing the ablation procedure when the increase in conduction time discontinues.

22. The method of claim 18, further comprising:

transmitting a first signal from the first electrode at a first time prior to ablation;

receiving the first signal at the second electrode at a second time prior to ablation; and taking the difference between the second time and the first time as a baseline conduction time.

23. The method of claim 18, wherein determining the effectiveness of a tissue ablation procedure as a function of the measurements of conduction time comprises:

monitoring change in conduction time with the measurements; and determining the full thickness of the tissue has been ablated when the conduction time reaches a maximum value.

24. The method of claim 23, further comprising discontinuing the ablation procedure when the conduction time reaches a maximum value.

25. A method for determining the effectiveness of a tissue ablation procedure, the method comprising:

prior to ablation, disposing a first electrode on a first side of tissue to be ablated and disposing a second electrode on a second side of the tissue, the second side being opposite the first side following ablation;

during the ablation procedure, making a plurality of measurements of impedance with the first electrode and the second electrode; and determining the effectiveness of a tissue ablation procedure as a function of the measurements of impedance.

26. The method of claim 25, wherein determining the effectiveness of a tissue ablation procedure as a function of the measurements of impedance comprises:

monitoring a decrease in impedance with the measurements; and determining the full thickness of the tissue has been ablated when the decrease in impedance discontinues.

27. The method of claim 26, further comprising discontinuing the ablation procedure when the decrease in impedance discontinues.

28. The method of claim 25, further comprising measuring a baseline impedance with the first electrode and the second electrode prior to ablation.

29. The method of claim 25, wherein determining the effectiveness of a tissue ablation procedure as a function of the measurements of impedance comprises:

monitoring change in impedance with the measurements; and determining the full thickness of the tissue has been ablated when impedance reaches a minimum value.

30. The method of claim 29, further comprising discontinuing the ablation procedure when impedance reaches a minimum value.

31. A method for determining the effectiveness of a tissue ablation procedure, the method comprising:

prior to ablation, disposing a first electrode on a first side of tissue to be ablated and disposing a second electrode on a second side of the tissue, the second side being opposite the first side following ablation;

during the ablation procedure, making a plurality of measurements as a function of the capacitance of the tissue with the first electrode and the second electrode; and determining the effectiveness of a tissue ablation procedure as a function of the measurements.

32. The method of claim 31, wherein determining the effectiveness of a tissue ablation procedure as a function of the measurements:

making a plurality of measurements of an alternating current phase angle with the first electrode and the second electrode;

monitoring a change in the magnitude of the phase angle with the measurements; and determining the full thickness of the tissue has been ablated when the change in the magnitude of the phase angle discontinues.

33. The method of claim 32, wherein monitoring a change in the magnitude of the phase angle comprises monitoring a decrease in the magnitude of the phase angle.

34. The method of claim 32, further comprising discontinuing the ablation procedure when the change in the magnitude of the phase angle discontinues.

35. The method of claim 32, further comprising measuring a baseline phase angle with the first electrode and the second electrode prior to ablation.

36. The method of claim 31, wherein determining the effectiveness of a tissue ablation procedure as a function of the measurements comprises:

monitoring a change in the magnitude of an alternating current phase angle with the measurements; and determining the fill thickness of the tissue has been ablated when the magnitude of the phase angle reaches a minimum value.

37. The method of claim 36, further comprising discontinuing the ablation procedure when the magnitude of the phase angle reaches a minimum value.

* * * * *